(12) United States Patent
Gruenbacher et al.

(10) Patent No.: US 7,744,232 B2
(45) Date of Patent: Jun. 29, 2010

(54) DECORATIVE LUMINARY

(75) Inventors: Dana Paul Gruenbacher, Fairfield, OH (US); Steven Anthony Horenziak, Cincinnati, OH (US); Steven Louis Diersing, Cincinnati, OH (US); Carl Eric Kaiser, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 396 days.

(21) Appl. No.: 11/717,960

(22) Filed: Mar. 14, 2007

(65) Prior Publication Data

US 2007/0230189 A1    Oct. 4, 2007

Related U.S. Application Data

(63) Continuation-in-part of application No. 29/269,367, filed on Nov. 28, 2006, now Pat. No. Des. 561,929, and a continuation-in-part of application No. 29/269,358, filed on Nov. 28, 2006, now Pat. No. Des. 565,239, and a continuation-in-part of application No. 29/269,333, filed on Nov. 28, 2006, now Pat. No. Des. 565,783.

(60) Provisional application No. 60/782,112, filed on Mar. 14, 2006, provisional application No. 60/861,467, filed on Nov. 28, 2006.

(51) Int. Cl.
  *F21V 1/00*   (2006.01)
(52) U.S. Cl. ........................................ 362/96
(58) Field of Classification Search .................... 362/96
  See application file for complete search history.

(56) References Cited

U.S. PATENT DOCUMENTS

| 674,980 | A | 5/1901 | O'Herron |
| 3,761,702 | A | 9/1973 | Andeweg |
| 3,890,085 | A | 6/1975 | Andeweg |
| 3,948,445 | A | 4/1976 | Andeweg |
| 4,009,384 | A | 2/1977 | Holland |
| 4,346,059 | A | 8/1982 | Spector |
| 4,493,011 | A | 1/1985 | Spector |
| 4,593,232 | A | 6/1986 | McEdwards |
| 5,097,180 | A | 3/1992 | Ignon et al. |

(Continued)

FOREIGN PATENT DOCUMENTS

JP            283439        10/1999

(Continued)

OTHER PUBLICATIONS

Found on p. 87 of a Mar. 31, 1996 Japanese catalogue called "Made for Export.".

(Continued)

*Primary Examiner*—Laura Tso
(74) *Attorney, Agent, or Firm*—Julia A. Glazer; Leonard W. Lewis; Steven W. Miller

(57) ABSTRACT

Decorative luminary for providing an aesthetically pleasing ambiance. The decorative luminary may include a shade. The shade may be disposable. The decorative luminary may also include a base. A light source may also be included as well. The present invention also relates to a method for making a decorative luminary of the present invention.

5 Claims, 15 Drawing Sheets

U.S. PATENT DOCUMENTS

| | | |
|---|---|---|
| 5,863,108 A | 1/1999 | Lederer |
| 5,876,678 A | 3/1999 | Harrell et al. |
| 5,908,231 A | 6/1999 | Huff |
| 6,120,737 A | 9/2000 | Zembrodt |
| 6,196,706 B1 | 3/2001 | Cutts |
| 6,254,248 B1 | 7/2001 | McAuley et al. |
| 6,364,501 B1 | 4/2002 | Tai |
| 6,465,420 B1 | 10/2002 | Perring et al. |
| 6,554,448 B2 | 4/2003 | Carpenter et al. |
| 6,619,559 B2 | 9/2003 | Wohrle |
| 6,783,117 B2 | 8/2004 | Wohrle |
| 6,966,665 B2 | 11/2005 | Limburg et al. |
| 2001/0040800 A1 | 11/2001 | Carpenter et al. |
| 2001/0043467 A1 | 11/2001 | Carpenter et al. |
| 2003/0107139 A1 | 6/2003 | Wohrle |
| 2003/0210555 A1 | 11/2003 | Cicero et al. |
| 2003/0231488 A1 | 12/2003 | Albee |
| 2004/0136888 A1 | 7/2004 | Shimizu et al. |
| 2004/0141315 A1 | 7/2004 | Sherburne |
| 2004/0196658 A1 | 10/2004 | Fung |
| 2005/0074358 A1 | 4/2005 | Hart et al. |
| 2005/0169666 A1 | 8/2005 | Porchia et al. |
| 2005/0169812 A1 | 8/2005 | Helf et al. |
| 2005/0185392 A1 | 8/2005 | Walter et al. |
| 2005/0285538 A1 | 12/2005 | Jaworski et al. |
| 2006/0002102 A1 | 1/2006 | Leonard |
| 2006/0115386 A1 | 6/2006 | Michaels et al. |
| 2007/0122373 A1 | 5/2007 | Woo et al. |

FOREIGN PATENT DOCUMENTS

| | | |
|---|---|---|
| WO | WO 2004-093929 | 11/2004 |
| WO | WO 2006-023858 | 3/2006 |

OTHER PUBLICATIONS

From the website of the Fern Group, Ltd. of Toronto, Canada, web address: http://www.ferngroup.corn/index.php?option=com_virtuemart&Itemid=43, downloaded on Aug. 28, 2008, 2 pages.

U.S. Appl. No. 29/269,367, filed Nov. 28, 2006 Meeker et al.

U.S. Appl. No. 29/269,358, filed Nov. 28, 2006 Meeker et al.

U.S. Appl. No. 29/269,333, filed Nov. 28, 2006 Meeker et al.

International Searching Authority, International Search Report, International application No. PCT/US2007/006515, European Patent Organisation, 9 pages.

Brookstone, Innovations for Home and Life—Flameless Wax Sensor Candle www.brookstone.com/store/productasp?product_code=507202&search_type=search, printed Jan. 9, 2007.

Brookstone, Innovations for Home and Life—Flameless Aromatic Candle www.brookstone.com/store/product.asp?product_code=541482&search_type=search, printed Jan. 9, 2007.

DECORATIVE LUMINARY

CROSS REFERENCE TO RELATED APPLICATIONS

This application claims the benefit of U.S. Provisional Application Ser. No. 60/782,112, filed Mar. 14, 2006 and U.S. Provisional Application Ser. No. 60/861,467 filed Nov. 28, 2006 and is a continuation-in-part of U.S. application Ser. No. 29/269,367 filed Nov. 28, 2006 now U.S. Pat. No. D,561,929, U.S. application Ser. No. 29/269,358 filed Nov. 28, 2006 now U.S. Pat. No. D,565,239, and U.S. application Ser. No. 29/269,333 filed Nov. 28, 2006 now U.S. Pat. No. D,562,783.

FIELD

The present invention relates to a decorative luminary for providing an aesthetically pleasing ambiance.

BACKGROUND

It is known in the art to utilize scented candles for providing a pleasing ambiance. However, scented candles can be messy and can also pose concerns related to the utilization of an open flame. The present invention overcomes these limitations. The decorative luminary of the present invention provides an aesthetically pleasing ambiance. It does not utilize a flame, hence eliminating concerns pertaining to the use of an open flame. Furthermore, as the decorative luminary is not waxed-based, there is no concern with the dripping and messiness that can be associated with scented candles. Yet further, the luminary of the present invention offers the user flexibility as the shade of the luminary is easily interchangeable and disposable thereby providing the user with choices as to scents and decorative styles.

This and other features, aspects, advantages, and variations of the present invention will become evident to those skilled in the art from a reading of the present disclosure with the appended claims and are covered within the scope of the claims.

SUMMARY OF THE INVENTION

In one aspect, the present invention relates to a decorative luminary. The decorative luminary may comprise a base, a light source, and one or more disposable shades. The shade may be impregnated with a composition wherein from about 50% to about 100% is comprised of a volatile composition wherein the volatile composition includes at least one ingredient which has a Kovat's Index from about 600 to about 1800.

The disposable shade may be impregnated with a volatile composition comprising perfume ingredients wherein the perfume ingredients are selected from a first group of ingredients having a boiling point of about 20° C. to about 250° C. and a ClogP value from about −2 to about 3; a second group of ingredients having a boiling point of about 20° C. to about 250° C. and a ClogP value from about 3 to about 9; a third group of ingredients having a boiling point of about 250° C. to about 400° C. and a ClogP value from about −2 to about 3; a fourth group of ingredients having a boiling point of about 250° C. to about 400° C. and a ClogP of about 3 to about 9; or a combination thereof.

The disposable may include a volatile composition wherein the volatile composition is about 50% or more depleted from the shade within about twenty-four hours after the shade is exposed to air. The disposable shade may be comprised of a material having a fluid holding capacity of about 5 ml/m² to about 1000 ml/m² and an average pore size of about 0.1 microns to about 100 microns.

In another aspect of the invention, there is provided a composition for a decorative luminary. The composition comprises a volatile composition wherein the volatile composition is provided in an amount capable of adding from about 60 milligrams to about 15 grams of the volatile composition to a disposable shade. Prior to addition to the disposable shade, the volatile composition is contained in an ampoule, a pouch, a dropper bottle, a sachet, a spray, a blow-fill seal container, or a combination thereof. The volatile composition may have a Kovat's Index of about 600 to about 1800.

In yet another aspect of the invention, a decorative luminary, comprises a base and a disposable shade. The shade is associated with the base. The base includes a connecting element and the shade includes a reciprocal connecting element whereby the connecting element of the base contacts the reciprocal connecting element of the shade.

In another aspect of the invention, a disposable shade is provided wherein the shade is comprised of a material having a thickness of between about 0.008 mm and about 5 mm and wherein the shade includes a volatile composition.

In a further aspect of the invention, a decorative luminary is provided wherein the decorative luminary comprises a disposable shade and changing indicia.

In an additional aspect of the invention, a method for making a decorative luminary is provided. The method comprises the steps of:
  a) providing a base including a light source;
  b) providing a disposable shade; and
  c) associating the base with the disposable shade such that the base is in communication with the shade.

In another aspect of the invention, a method is provided for forming a decorative luminary including providing a disposable shade in a flat form or a substantially flat form; and expanding the disposable shade into a substantially non-flat form.

In a further aspect of the invention, a method is provided for a user to customize the components of a decorative luminary. The method comprises the steps of:
  a) providing an interactive sample display which includes each option of each decorative luminary component;
  b) providing a user access to the interactive sample display; and
  c) allowing a user to select which option of each decorative luminary component the user would like so as to allow the user to view a sample of the decorative luminary having incorporated therein each option of each decorative luminary component the user has selected.

BRIEF DESCRIPTION OF THE DRAWINGS

It is believed that the present invention will be better understood from the following description taken in conjunction with the accompanying drawings in which.

DETAILED DESCRIPTION

Figure 1:
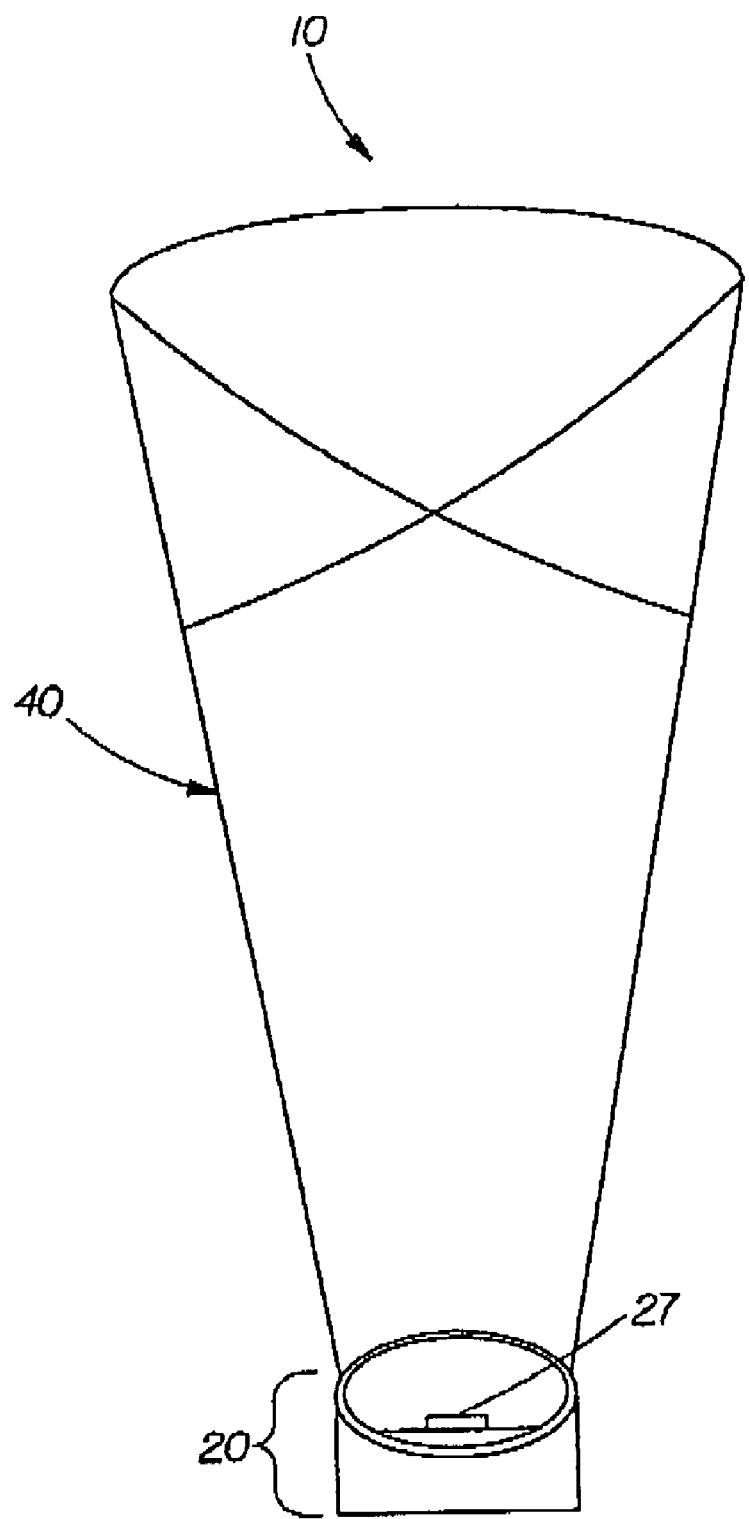
FIG. 1 is a perspective view of an embodiment of a decorative luminary made in accordance with the present invention.
Figure 2:
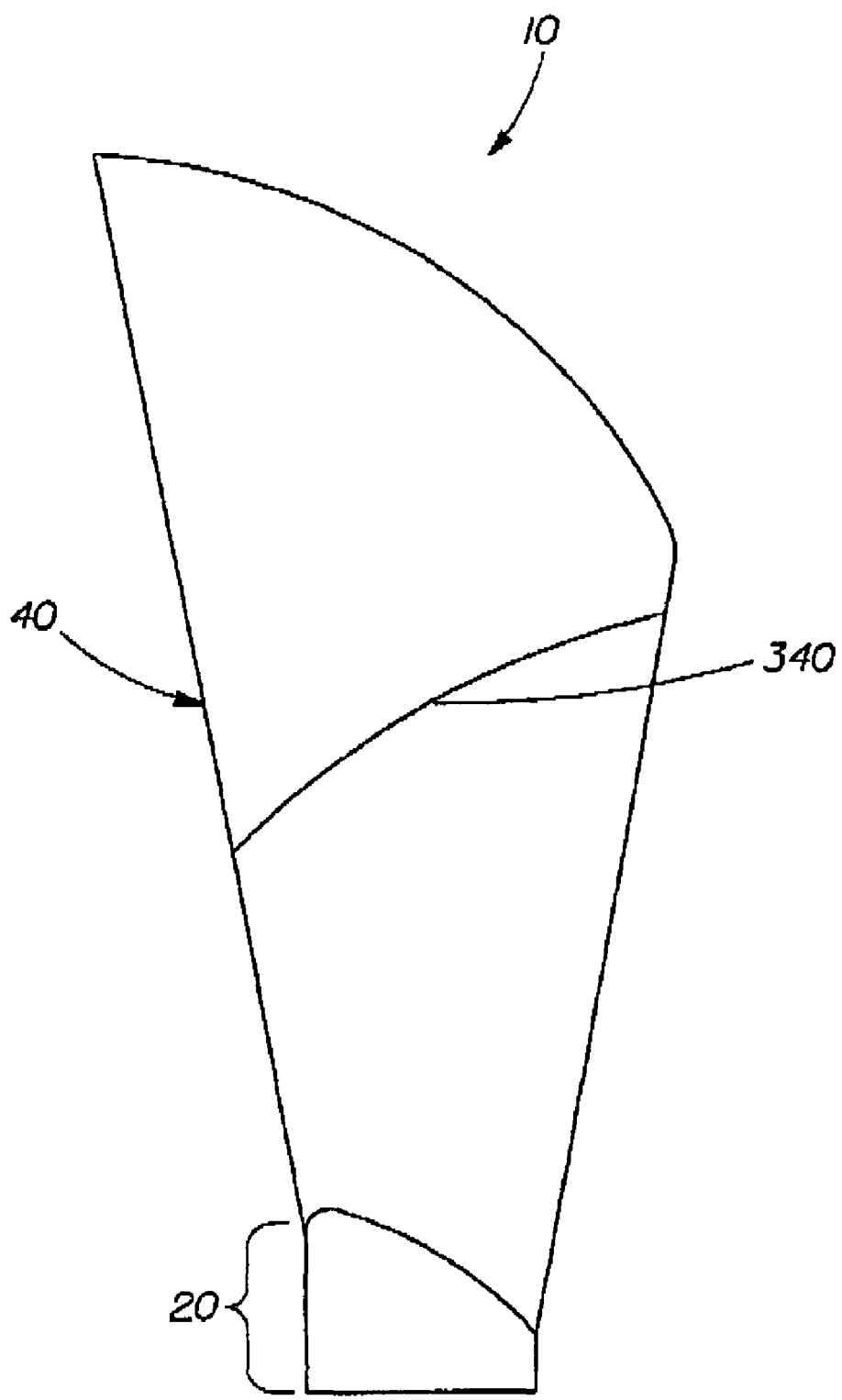
FIG. 2 is a side view of the decorative luminary shown in FIG. 1.
Figure 3:
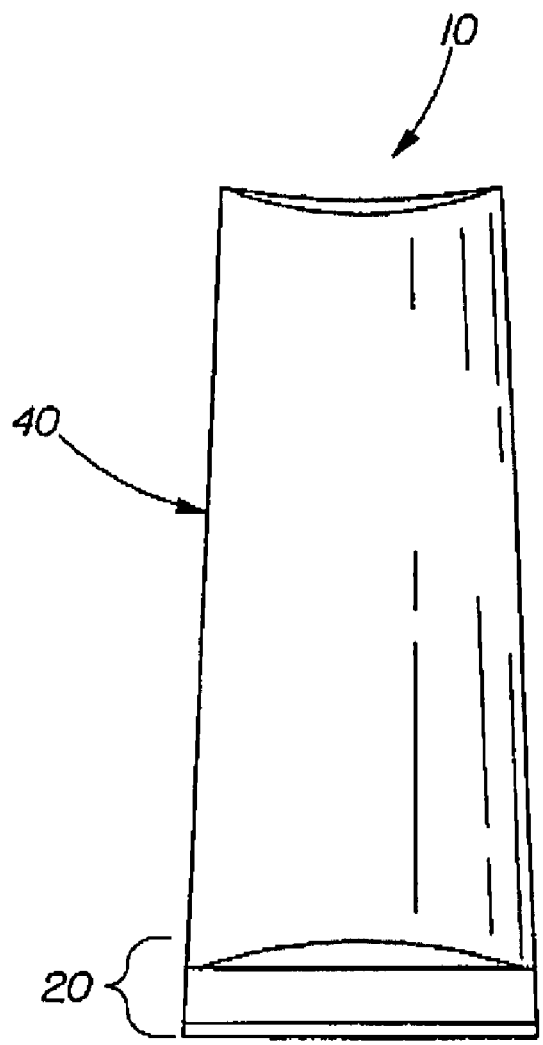
FIG. 3 is a perspective view of an embodiment of a decorative luminary made in accordance with the present invention.
Figure 4:
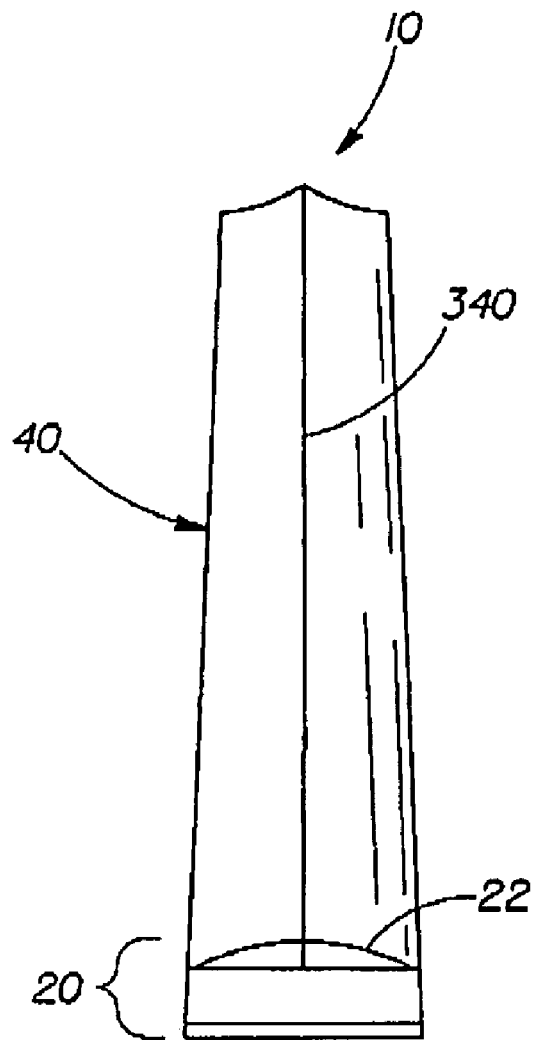
FIG. 4 is a side view of the decorative luminary shown in FIG. 3.
Figure 5:
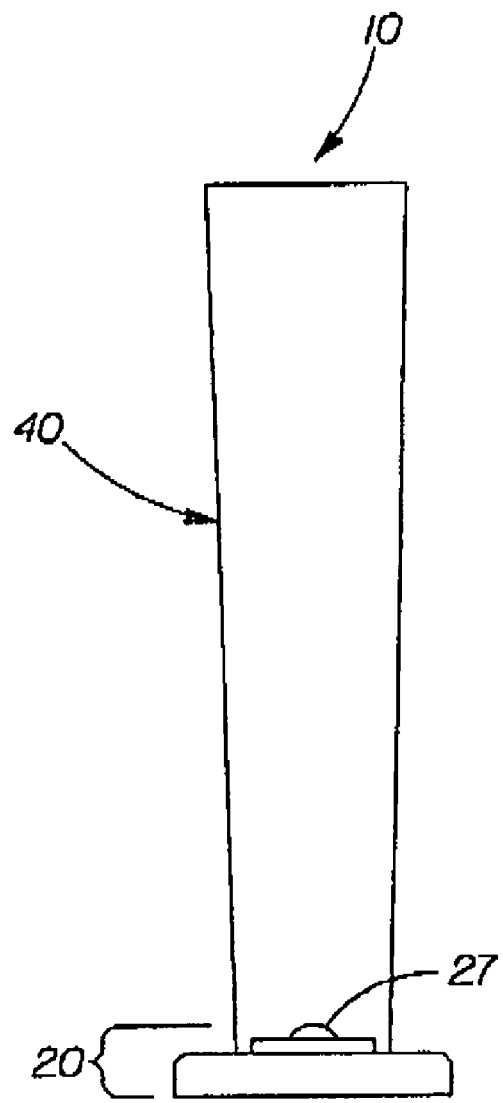
FIG. 5 is a perspective view of an embodiment of a decorative luminary made in accordance with the present invention.
Figure 6:
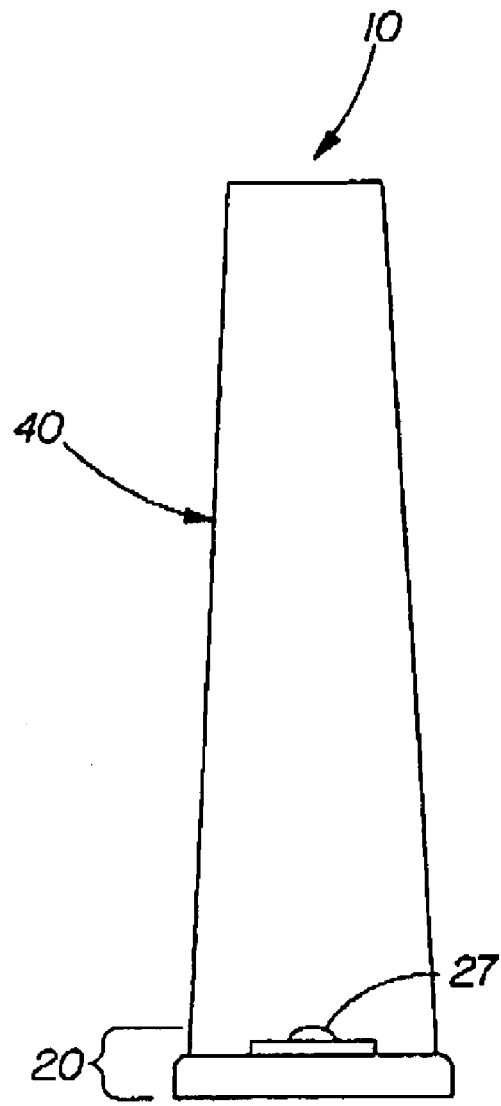
FIG. 6 is a side view of the decorative luminary shown in FIG. 5.

Reference will now be made in detail to various embodiments of the present invention, examples of which are illustrated in the accompanying drawings wherein like numerals indicate the same elements throughout the views. All percentages, ratios and proportions herein are on a weight basis unless otherwise indicated.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

As used herein, "disposable" refers to something which is discarded after a few uses.

As used herein "durable" refers to something which can be used many times.

As used herein, "indicia" refers to any desired array that creates an image or a pattern.

As used herein, "opacity" refers to an indication of how much light passes through a material. The higher the opacity, the less is the amount of light that passes through the material. Generally opacity is calculated from reflectance measurements of the material with a black backing and the same material with a white backing wherein:

% Opacity=$(Y_{black\ backing}/Y_{white\ backing})\times 100$ wherein Y is the CIE tristimulus value of Y.

As used herein, "volatile materials" refers to a material that is vaporizable.

As used herein, "volatile dyes," refers to soluble or insoluble coloring matter that is vaporizable. The chemical composition can be a single component or mixture.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Decorative Luminary

The decorative luminary of the present invention may comprise a base, a light, and a shade which encloses the light. The decorative luminary may also include a volatile composition which can be included separately and/or included with the base, the shade, or a combination thereof. The shade may be included with the base and/or with the light. Alternatively, it may be provided separately as a stand-alone article. The shade can include indicia. In one non-limiting example the indicia can undergo a visual transition during use.

A. Base

Referring to FIGS. 1-7, the decorative luminary 10 of the present invention may comprise a base 20. The base 20 may be sized and shaped to receive and support the shade 40. A light 27 may also be associated with the base. In the case where a light 27 is present a power supply 26 may also be present in order to provide power to the light 27 and/or switches which turn the light on and off. Any power supply 26 may be used including but not limited to batteries, household current, solar power, or the like. In the instance where batteries are used it may be desirable to optionally include an access panel such as a door so that the batteries may be easily accessed for replacement purposes. For instances, referring to FIG. 7, the bottom 23 of base 20 may serve as an access panel. Additionally, a volatile composition may be associated with the base 20. If desired, the base 20 may be decorated. Generally, the base 20 should be heavy enough to support the weight of the assembled decorative luminary 10 without tipping. The base 20 may be formed in any number of ways familiar to those of ordinary skill in the art, non-limiting examples of which include injection molding, compression molding, and thermoforming. The base 20 may comprise one or more polymers, one non-limiting example of which is thermoplastic polymers. Typically, the light/light source 27 is protected by utilizing a cover 22. Cover 22 if desirable can also function as a light diffuser to help diffuse the light from light/light source 27. In one non-limiting embodiment the cover 22 may be a thermoplastic cover such as a transparent thermoplastic cover that is resistant to different materials which may come into contact with the base 20 such as components of the volatile composition. One non-limiting example of a suitable polymer is injection molded grades of impact modified acrylonitrile available under the name of BAREX and manufactured by Innovene of Chicago, Ill. Other suitable materials include but are not limited to injection molding and/or thermoforming grades of styrene acrylonitrile ("SAN"), polypropylene, polyethylene terephthalate ("PET"), or combinations thereof.

Figure 13:
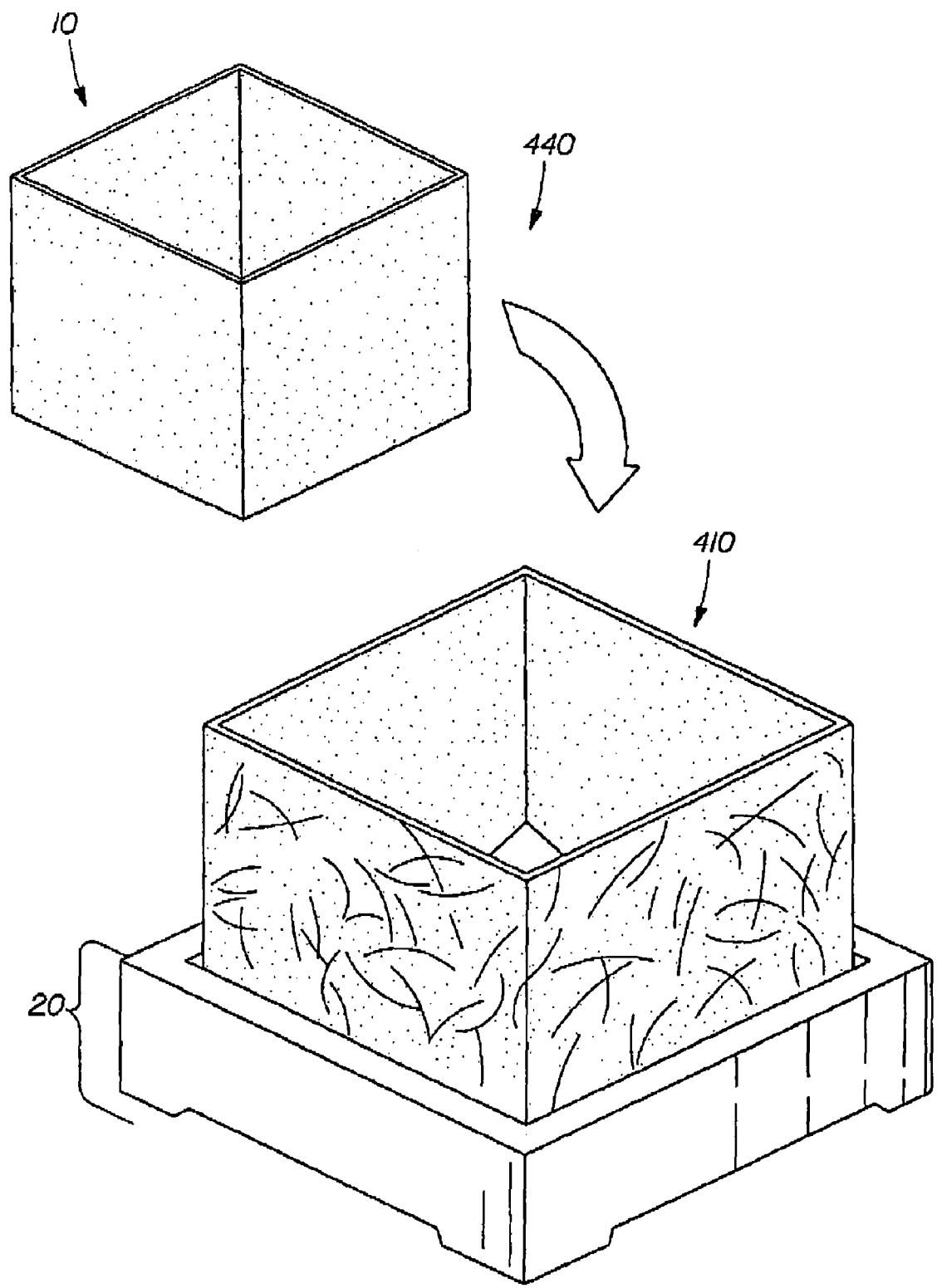
FIG. 13 is an exploded view of an embodiment of a decorative luminary made in accordance with the present invention.
Figure 14:
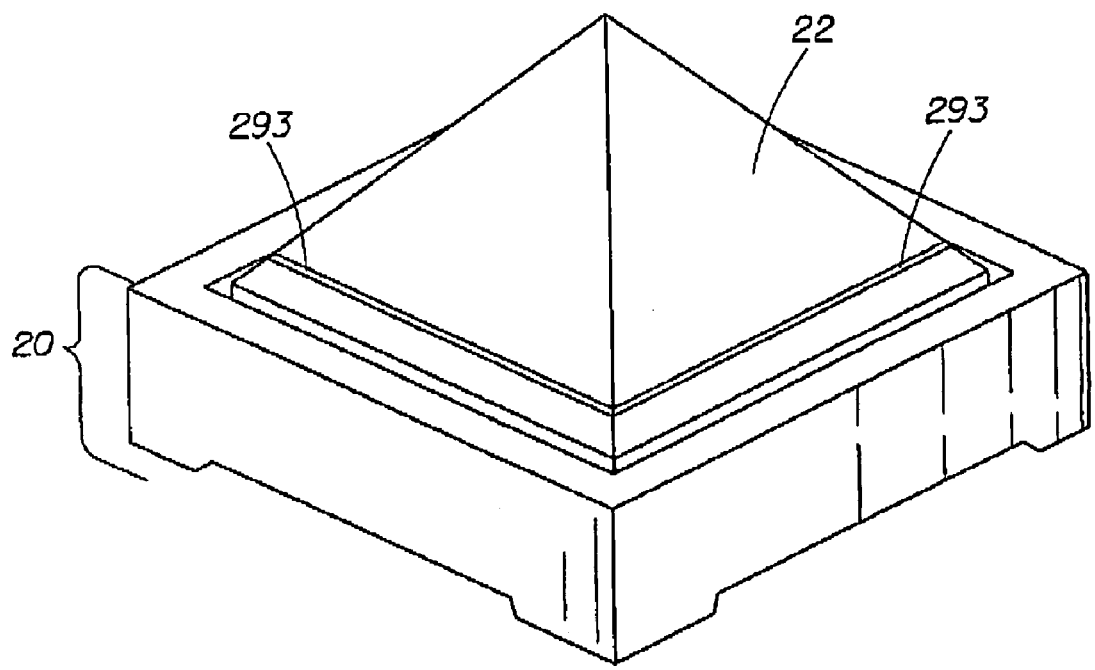
FIG. 14 is a perspective view of the base of the decorative luminary of FIG. 13.
Figure 15A:
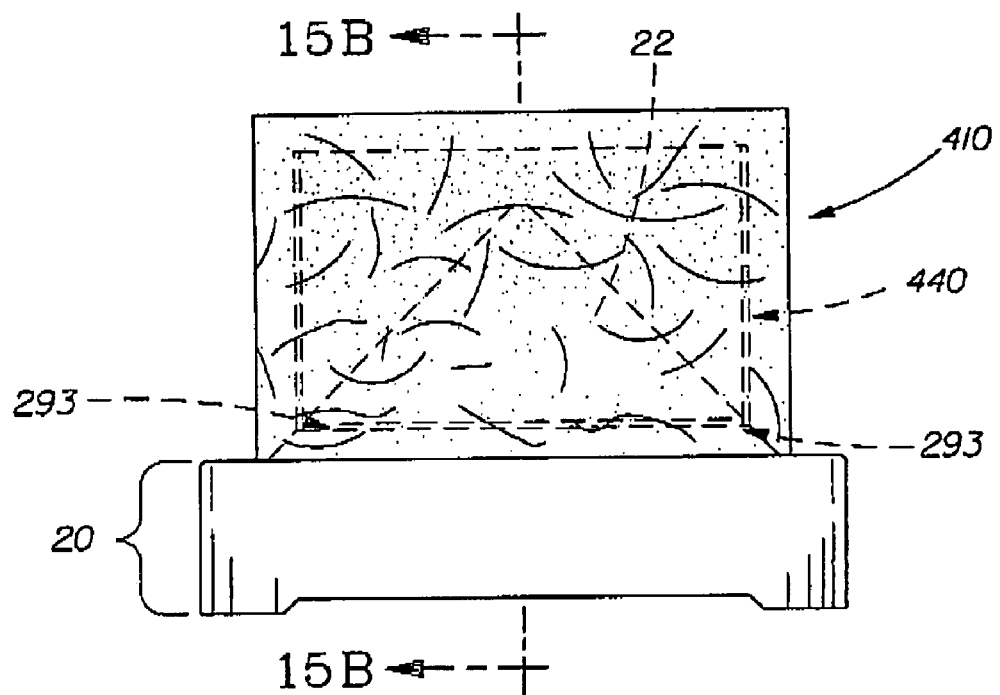
FIG. 15A is a side view of an embodiment of a decorative luminary.
Figure 15B:
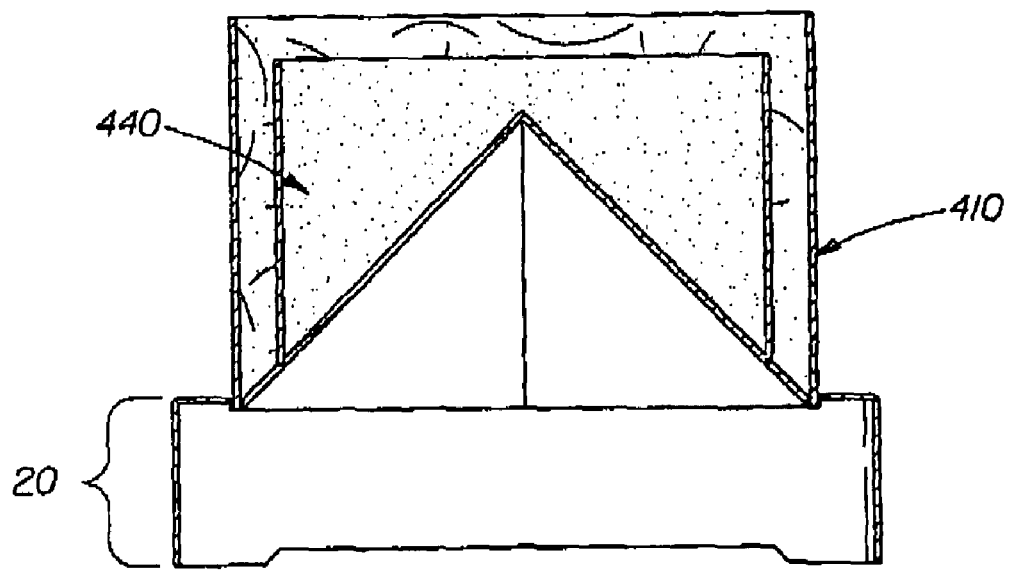
FIG. 15B is a cross sectional view taken along line 15-15 of the decorative luminary of FIG. 15A.

Referring to FIGS. 14 and 15, in one non-limiting embodiment it may be desirable to include a step or ledge 293 around either cover 22 (as shown) or around base 20 (not shown) in order to provide a resting area for the bottom portion of a shade such as shade 440. Alternatively, one or more members (not shown), non-limiting examples of which include pins and protrusions, could be included with cover 22 and/or base 20 which could be used to engage with a shade in order to hold the shade (such as shade 40, shade 410, or shade 440 shown in FIGS. 1-6, FIGS. 10-11, FIG. 13, and FIGS. 15-19) in place on the cover 22 and/or base 20. The members may be reciprocating or stationary, or a combination thereof. If desired, the shade may also include one or more reciprocating members which may be designed to engage with the reciprocating member(s) of the cover 22 and/or base 20. In addition to or alternatively, if desired, the reciprocating member included with cover 22, base 20, and/or the shade 40 could serve as a switch so that when the reciprocating member is engaged, the light of the decorative luminary is activated.

B. Light

Figure 7:
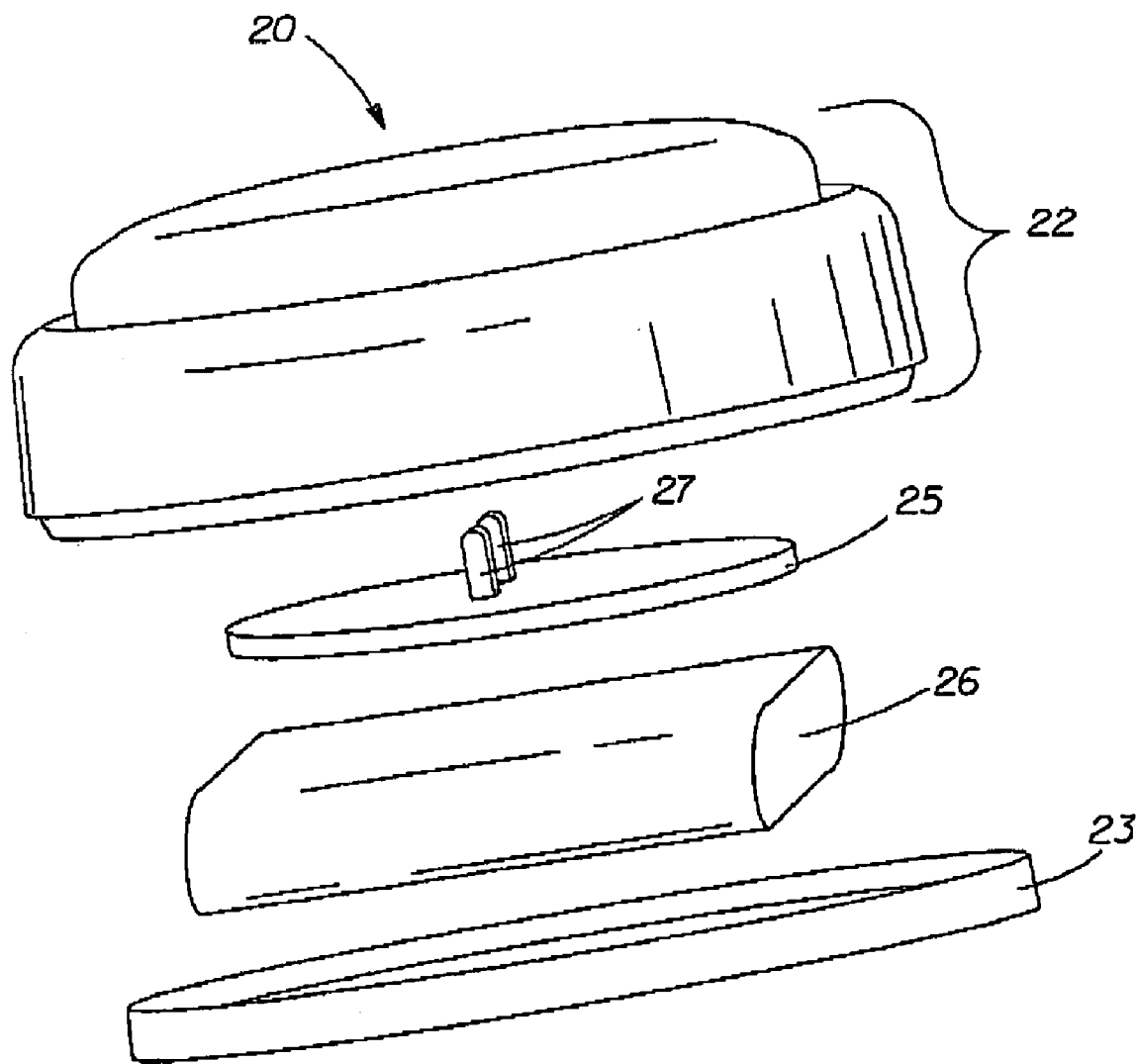
FIG. 7 is an exploded view of an embodiment of a base for a decorative luminary made in accordance with the present invention.

Referring to FIGS. 1-7, the present invention may also include a light/source of light 27. Generally, the source of the light 27 will be associated with the base 20 though it could be located in other areas including but not limited to the shade 40. Furthermore, if desired there could be more than one light/light source 27 such as shown in FIG. 7. Suitable light sources include but are not limited to light emitting diodes ("LEDs"), incandescent sources of light including but not limited to filament-based bulbs, and luminescent sources of light including but not limited to electroluminescent, chemiluminescent, cathodoluminescent, triboluminescent, and photoluminscent materials.

In one non-limiting embodiment the light source is one or more LEDs. The LED can be any number of colors including but not limited to yellow, white, red, green, blue, pink, or a combination thereof. One non-limiting example of an LED suitable for use with the present invention is part No. MV8305 (available from Fairchild Semiconductor of South Portland, Me.).

In one non-limiting embodiment of the present invention, the light 27 is mounted on mounting 25 present in the base 20 of the decorative luminary 10 as shown in FIG. 7. It may be designed such that the light 27 turns on automatically when the shade 40 contacts the base 20. This may be accomplished in any number of ways, one non-limiting example of which is utilizing a surface mounted contact switch (not shown) that is engaged when the shade 40 contacts the base 20. If desired, the light source could be connected to a timer (not shown) incorporated in the base 20 such that the light 27 automatically turns-off after a predetermined time period after the shade 40 is placed in contact with the base 20. In another non-limiting embodiment (now shown) the light source may be present in the shade 40. This could be accomplished in any number of ways. For instance, a surface mounted contact switch (not shown) could be mounted on the shade 40 such that when the shade 40 contacts the base 20, a light 27 turns on. Alternatively, electroluminescent and/or chemiluminescent materials could be used as the light source. In one non-limiting example, electroluminescent materials are provided either as part of the shade 40, as part of the base 20, or a combination thereof. For instance, the shade 40 and/or the base 20 could be made in whole or in part from electroluminescent material. One non-limiting example of electroluminescent material suitable for use with the present invention is EL available from Novatech Electroluminescent Incorporated of Chino, Calif.

In yet another non-limiting embodiment, an absorbent and/or porous shade 20 could be impregnated with phenyl oxalate ester with a fluorescent dye. A rupturable pouch containing hydrogen peroxide could be included with the shade 20. A user would then rupture the pouch thereby allowing the hydrogen peroxide contact the phenyl oxalate ester/dye. Contact of the hydrogen peroxide contained in the pouch with the phenyl oxalate ester/dye impregnated in the shade 20 would provide light via the chemiluminescent reaction between the two materials.

Figure 8A:
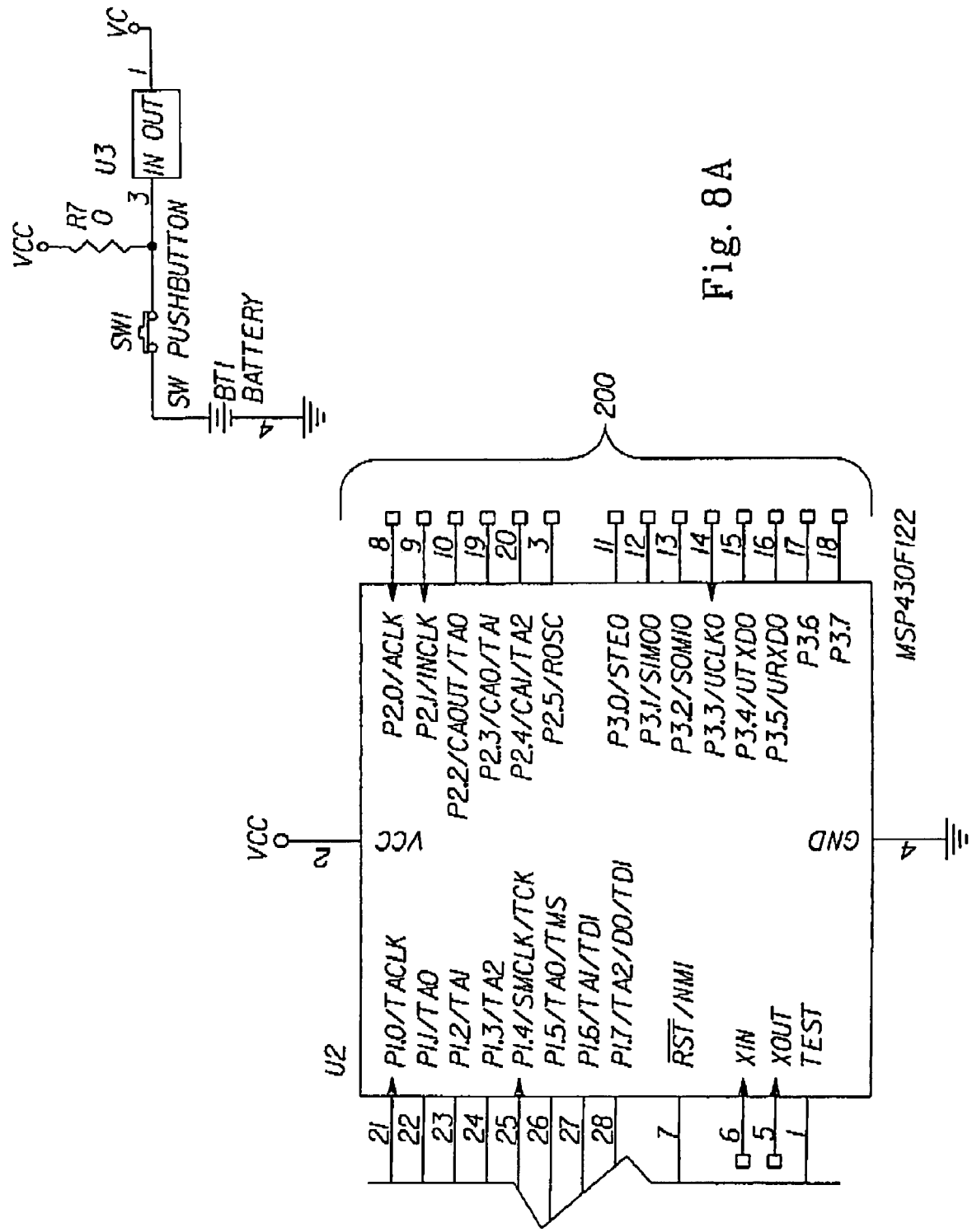
FIG. 8 is an electrical schematic diagram of an embodiment of a light source for a decorative luminary made in accordance with the present invention.
Figure 8B:
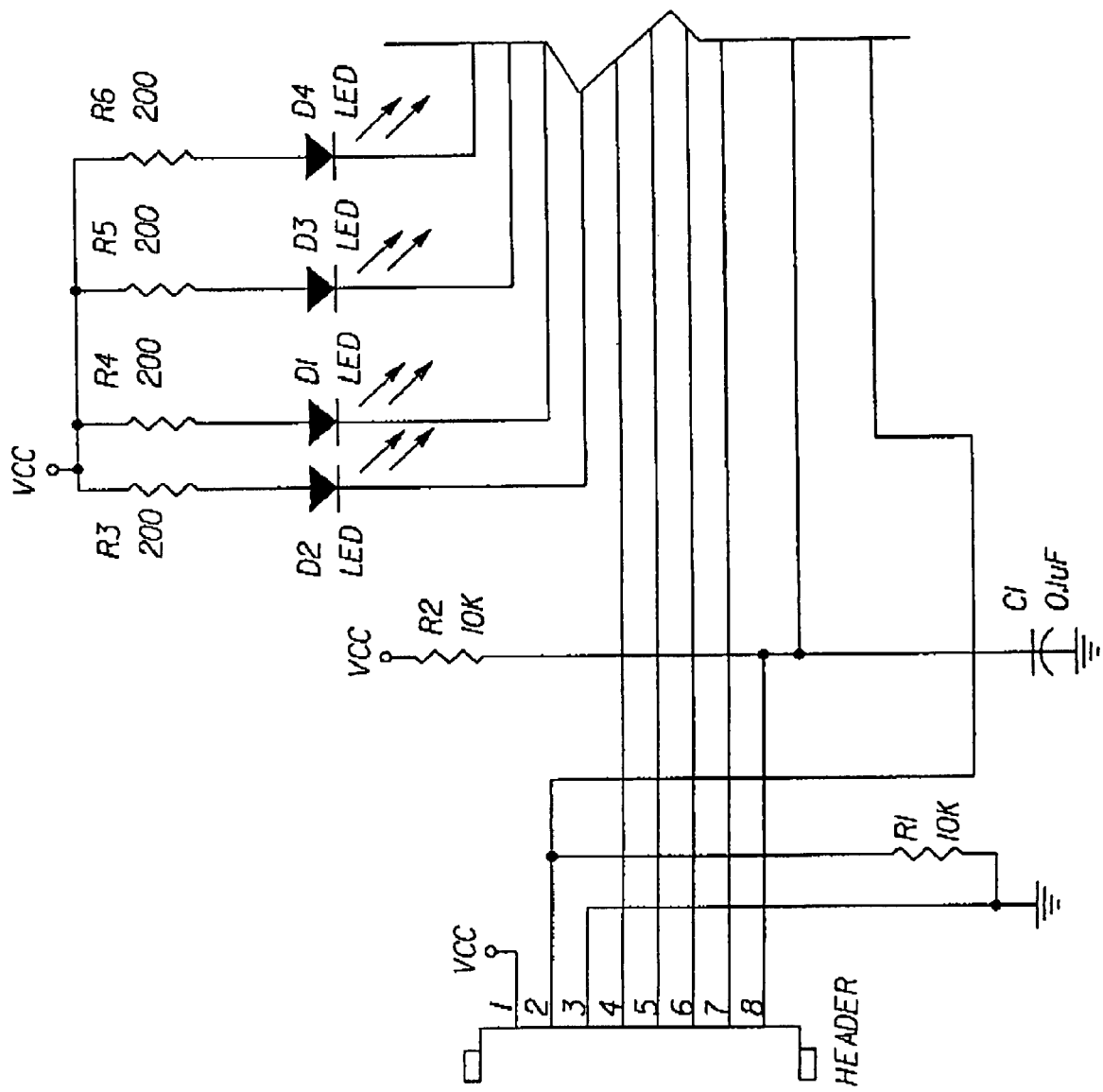

If desired, the light source may provide a light that is varying in intensity. The light source may be associated with a power source (non-limiting examples of which include batteries and/or an AC power source), a microcontroller, a switch, and one or more LEDs. One non-limiting example of a microcontroller suitable for use with the present invention is Part. No. MSP430F122, available from Texas Instruments of Dallas, Tex. The light intensity may be varied by the microcontroller using Pulse Width Modulation ("PWM"). PWM refers to the process of instantaneously controlling digitally the amount of power being delivered to the LEDs. FIG. 8 is illustrative of one non-limiting example of an electrical schematic diagram which depicts circuitry suitable for controlling the light source of the present invention. Referring to FIG. 8, microcontroller 200 may be programmed to execute an algorithm to vary the LED intensity. In essence, microcontroller 200 can be programmed to closely mimic the visual characteristics such as intensity and motion of the flame of a candle. For example, a typical candle flame generally has a substantial amount of left to right motion which produces variations in light intensity. Microcontroller 200 used to control the light source of the present invention may be programmed to capture the variations in light intensity. For example, the left to right motion may be captured by placing two LEDs side by side and using pulse width modulation to vary the intensity and motion. In an alternate non-limiting example, microcontroller 200 may be programmed to vary the intensity of the LEDs in a random fashion. In another example, microcontroller 200 may be programmed to increase or decrease the intensity of the LEDs over time.

C. Shade

Referring to FIGS. 1-7, the decorative luminary 10 of the present invention also comprises a shade 40. The shade 40 may be included in conjunction with the base 20 and/or in conjunction with the light source. Alternatively, the shade 40 may be provided separately as a stand-alone article. It is desirable that the shade 40 of the present invention be disposable. The shade 40 may be a single use disposable shade 40 or alternatively can be a disposable shade 40 designed for more than one use. Alternatively as shown in FIGS. 13-15 the decorative luminary 10 may comprise a more durable outer shade 410 and a disposable inner shade 440. In one non-limiting example outer shade 410 could be a durable decorative shade while inner shade 440 could be a disposable shade used to deliver scent without having to dispose of outer shade

410. As inner shade 440 would be disposable, it could be easily interchanged to allow a user to experience different scents if desired.

Typically, when used in conjunction with the light source, the shade 40 surrounds a substantial portion of the light source. For example, the shade 40 surrounds at least about 90° around the light source, or at least about 180° around the light source, or completely surrounds the light source.

The shade 40 comprises a substrate. The substrate can be made of a single material or a combination of material. The shade 40 can be transparent, translucent, opaque, or a combination thereof. Generally, the shade 40 is made from any material or combination of materials that will let light pass through some portion of the substrate and that is stiff enough to hold a shape. A non-limiting list of suitable materials include cellulosic materials, non-cellulosic materials, and combinations thereof. Non-limiting examples of these include thermoplastics including but not limited to foamed thermoplastics and polyolefinic-based materials including but not limited to polyethylene, polypropylene, and ethylene vinyl acetate ("EVA"); and thermosets including but not limited to polyurethanes; paper; vellum; parchment; leather; woven materials; and non-wovens. One suitable non-woven is SYNERGEX 6130 available from BBA/Fiberweb of Simpsonville, S.C.

Figure 9:
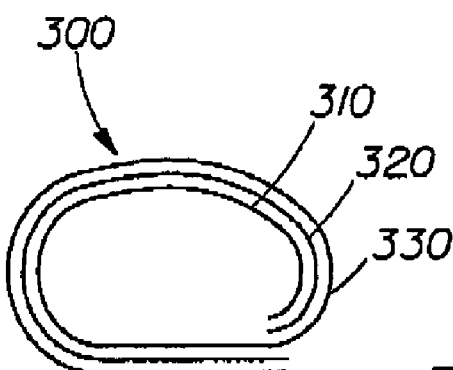
FIG. 9 is a top sectional view of an embodiment of a substrate material made in accordance with the present invention.
Figure 10:
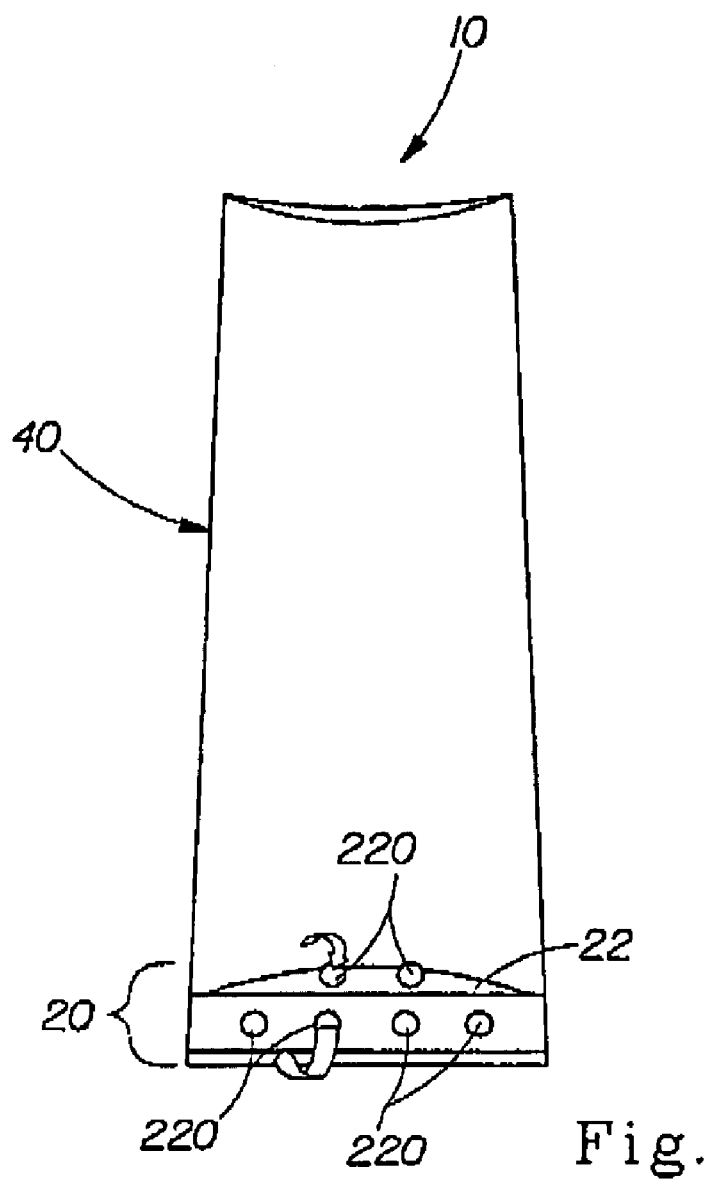
FIG. 10 is a perspective view of an embodiment of a decorative luminary made in accordance with the present invention.
Figure 11:
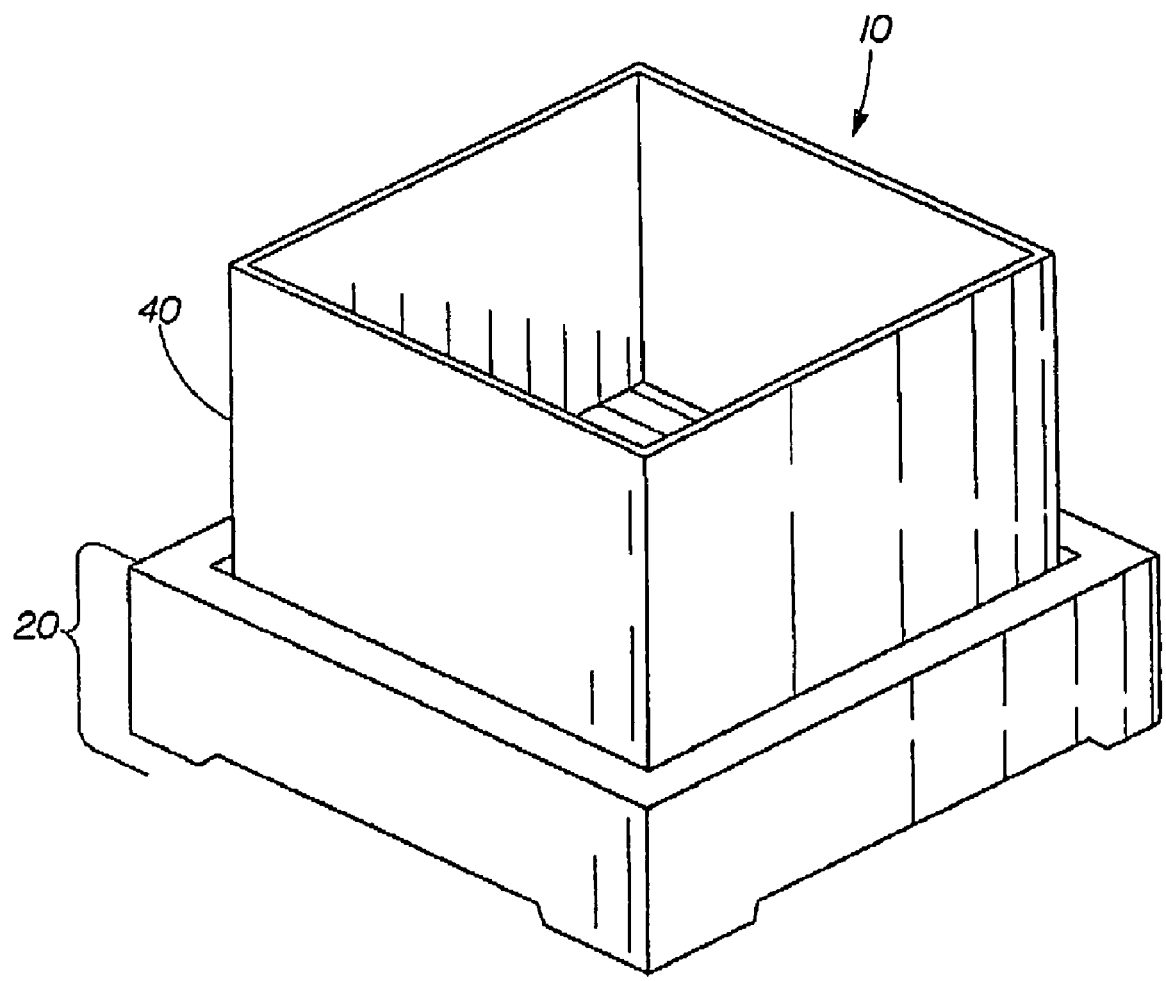
FIG. 11 is a perspective view of an embodiment of a decorative luminary made in accordance with the present invention.

The shade 40 can be comprised of one or more layers of material 300 such as shown in FIG. 9. Each layer may comprise one or more types of materials. Each layer of the shade typically has a thickness of from about 0.008 mm to about 5 mm or from about 0.01 mm to about 1 mm with an average total thickness for the shade of from about 0.02 mm to about 5 mm or from about 0.04 mm to about 1 mm as measured with a hand-held thickness gauge such as Model No. 22P-10 available from Mahr-Federal of Providence, R.I.

The layers may be combined by any means known for creating layered flexible structures, non-limiting examples of which include adhesively combining, thermal or ultrasonic bonding, extrusion coating, extrusion laminating, or combinations thereof.

In one non-limiting embodiment, the shade 40 may include at least one layer of an absorbent material capable for example of holding a volatile composition without dripping or releasing due to gravity or capillary forces. Suitable absorbent materials include but are not limited to porous materials having a fluid holding capacity from about 5 ml/m$^2$ of shade material to about 1000 ml/m$^2$ or from about 10 ml/m$^2$ to about 400 ml/m$^2$. Suitable absorbent materials include but are not limited to fibrous cellulose-based materials, fibrous thermoplastic-based materials including but not limited to spunbond polypropylene, spunbond polyester, and the like, and other fibrous materials including but not limited to fiberglass, wherein the material has a pore volume of about 10% to about 95% or a pore volume about 20% to about 90% and an average pore size of from about 0.1 microns to about 100 microns or from about 0.3 microns to about 80 microns. Non-limiting examples of other suitable absorbent materials include foams made from thermoplastics one non-limiting example of which is open-celled polyethylene foam (such as those available from Sentinel Products Corporation of Hyannis, Mass.), urethane, cellulose and/or starch, and microporous polymer films with at least 20% open area for containing and releasing a volatile composition. Pore size distribution and the % pore volume can be measured, for example, by using a TRI autoporisimeter available from TRI/Princeton of Princeton, N.J. Examples of suitable absorbent materials include but are not limited to SYNERGEX 6130 manufactured by BBA/Fiberweb of Simpsonville, S.C. and GRADE 7020 manufactured by Cellutissue Corporation of East Hartford, Conn.

If desired, the absorbent material can be treated to be either hydrophilic, hydrophobic, oleophilic, or oleophobic, or a combination thereof so as to either aid in releasing a volatile composition or to aid in holding onto a volatile composition. If desired, all or some portion of the absorbent material could be treated. For instance, it may be desirable to treat the entire surface of the absorbent material or to just treat the edges so as to prevent or limit the migration of the volatile composition to the edges of the shade. For example, in one non-limiting scenario, treating about 5 mm to about 20 mm along the edges of the shade with an oleophobic coating could potentially help prevent predominately oil based perfume from migrating to the edges of the shade.

If desired, the shade could be constructed in two layers, wherein the outer layer consists of a barrier material which is substantially impermeable to for example a liquid volatile composition impregnated in the inner layer. The outer layer could serve to help minimize contact between the user and the volatile composition impregnated in the inner layer. Alternatively, the shade 40 could be constructed in three layers as shown in FIG. 9, wherein the inner layer 310 could comprise an absorbent material impregnated with a volatile composition, the middle layer 320 could comprise a barrier material which is substantially impermeable to the volatile composition impregnated in the inner layer 310, and the outer layer 330 could comprise a second material, non-limiting examples of which include porous material, non-porous material, or combinations thereof. Suitable barrier materials include but are not limited to non-porous films, such as low density polyethylene, high density polyethylene, polypropylene, polyester, ethylenevinyl alcohol ("EVOH"), aluminum oxide coated polyester, silicon dioxide coated polyester, metalized polyester a suitable example of which is PET, or combinations thereof. The barrier layer is typically from about 0.005 mm to about 1 mm in thickness or from about 0.01 mm to about 0.1 mm in thickness to maintain flexibility of the shade 40. In another variation of this embodiment, the middle barrier layer could be omitted.

In yet another embodiment (not shown), a volatile composition could be located on a discrete substrate that is separate from but connected to the shade 40. The discrete substrate may optionally be in the form of a patch or label. In one non-limiting embodiment, the discrete substrate may be more absorbent and thicker than the shade 40 so as to allow the discrete substrate to contain a higher percentage of a volatile composition in a smaller space or area. In addition a thicker discrete substrate may also serve to provide support and stability to the shade for example by attaching it to the bottom of the shade 40. One example of a suitable absorbent material which can be used for the discrete substrate is Product No. 7620W available from EMI Specialty Papers of Redding, Conn.

The shade 40 should be stiff enough to stand under its own weight and to easily fit over a base 20 (when used). Generally it is desirable that the shade 40 have a deflection force (i.e.; force needed to deflect a sample 3 mm wherein the sample has the dimensions of 50 mm in length, 12.7 mm in width and less than 1.6 mm in thickness as measured in accordance with ASTM D790-03 entitled "Flexural Properties of Unreinforced and Reinforced Plastics and Electrical Insulating Materials" using a span distance of 25.4 mm (as measured on an Instron Compression/Tensile Tester Model No. 550RC5451 manufactured by Instron Corporation of Norwood, Mass.) of between about 1 gram and about 200 grams or from about 5 grams to about 100 grams and a flexural modulus between about 0.1 gigapascals and about 10 gigapascals ("GPa").

The substrate comprising the shade 40 may be transparent, translucent, opaque, or a combination thereof. Typically, the materials comprising the shade 40 are selected so that at least a portion of the shade 40 when assembled appears translucent, transparent, or a combination thereof. Additionally, the shade 40 may include portions wherein the shade material is removed one non-limiting example of which is where patterns are die cut into the shade 40 and the die cut portions of material removed from the shade 40. The shade 40 may have an opacity ranging from about 0% to about 100%, or from about 20% to about 80%, or from about 25% to about 70%. The opacity of the substrate may vary from area to area and/or within a given time frame. For example, the shade 40 when partially wetted with a composition (a non-limiting example of which is a volatile composition such as a perfume), may have a particular opacity which will be different after evaporation of the composition. One suitable instrument which may be used for measuring opacity is the Hunter LabScan XE manufactured by Hunter Associates Laboratory of Reston, Va.

In one non-limiting embodiment the outwardly-facing side of the shade 40 is made of a material that has a natural appearance and is able to be printed or embossed with a pattern or image. In one embodiment a thin, flat material or combination of materials is folded into a tube-like shape and then bonded along one edge 340 to prevent the tube from unrolling as shown in FIGS. 1-7. If desired, the shade 40 can include creases to allow the shade 40 to be flattened. For example, for purposes of packaging, it may be desirable to provide the shade 40 to the consumer in a flattened or substantially flattened form. The consumer upon using can open the shade 40 and expand it to a non-flat form or substantially non-flat form, non-limiting examples of which include a cone, a tube, a sphere, a cube, a polygon, or any other shape.

If desired, the shades may be packaged individually in a high barrier pouch that will help to prevent volatile components of the composition from escaping. One suitable pouch material available from Sonoco Flexible Packaging of Franklin, Ohio comprises a lamination of acrylonitrile sealant film extrusion (sold under the tradename of BAREX) laminated to an aluminum foil barrier layer and a reverse printed PET outer layer. The BAREX sealant layer is desirable for its ability to minimize perfume absorption into the packaging sealant film. Non-limiting examples of other suitable sealant layers include but are not limited to blends or mono-layers of various polyolefins, EVOH, metalized polyester, and the like. Alternatively, it is possible to have multiple shades packaged into a high barrier recloseable pouch. The pouch can be made recloseable in any number of ways familiar to those of ordinary skill in the art including but not limited to utilizing a zip lock feature, adhesive tape, or a combination thereof.

Figure 17:
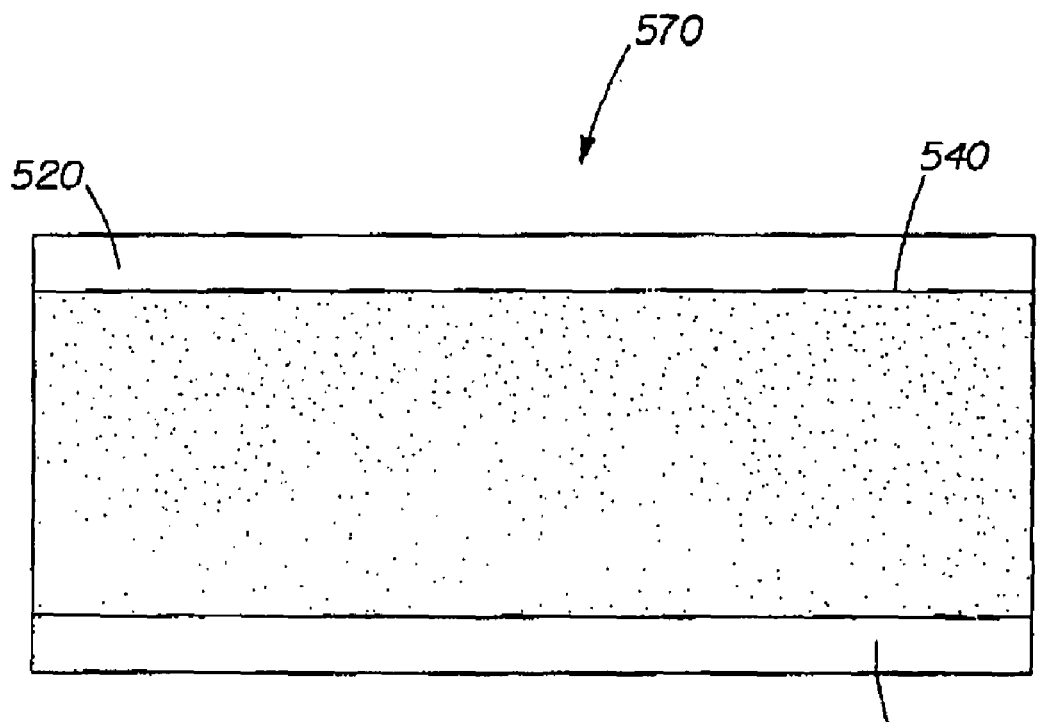
FIG. 17 is a front view of an embodiment of a shade made in accordance with the present invention.
Figure 18:
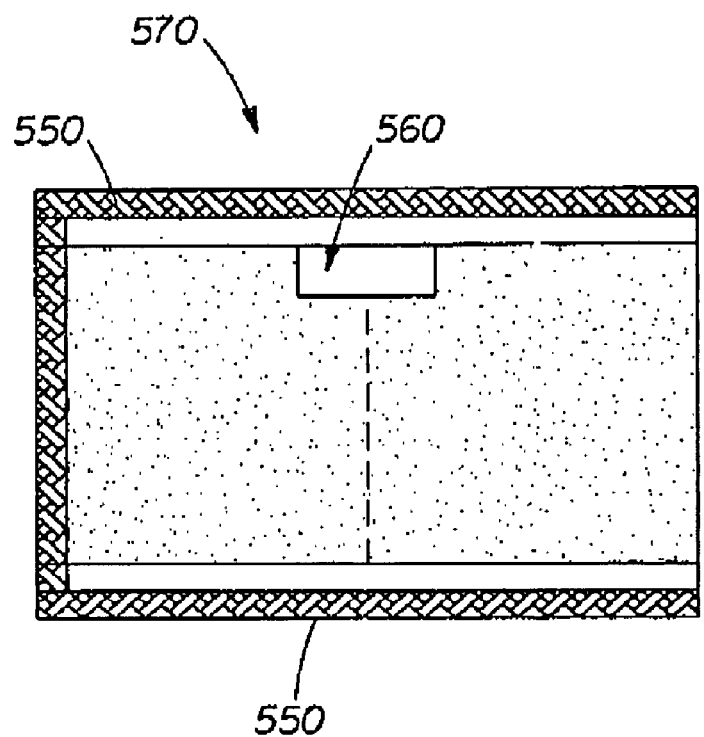
FIG. 18 is a front view of a shade of the shade of FIG. 17.
Figure 19:
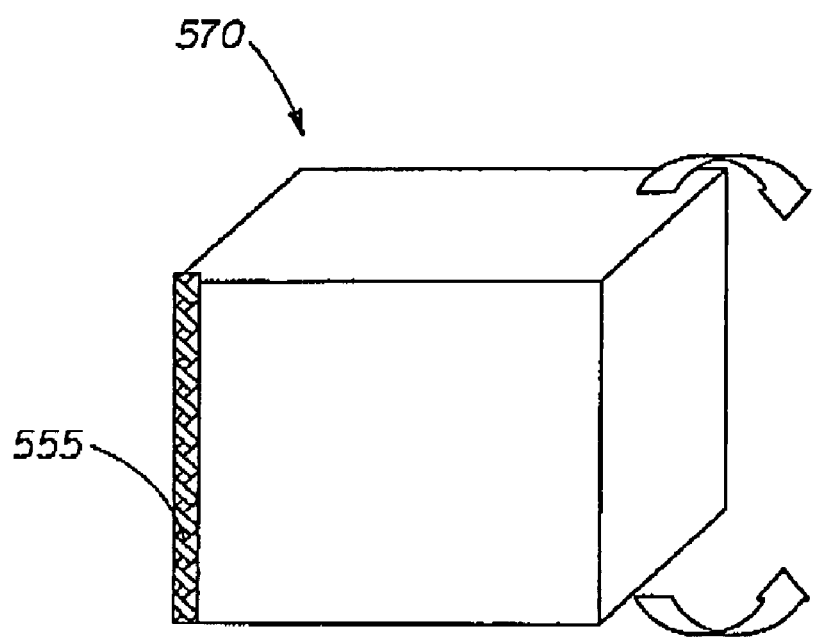
FIG. 19 is a perspective view of a shade of FIG. 17.

In another non-limiting example, it may be desirable to construct a shade wherein the shade and package are one unit as shown in FIGS. 17-19. This provides for an integral air freshening package without the need for separate packaging. As described previously, the shade may be constructed as a multi-layer system having an inner absorbent layer 540 and an outer barrier layer 520 as shown in FIG. 17. If desired, an additional decorative outer layer (not shown) could be optionally added to the outside of barrier layer 520. Barrier layer 520 may be comprised of a material suitable for preventing the migration of perfume to the outside as previously described. In the present example, barrier layer 520 also becomes the package layer to minimize perfume loss throughout the shelf-life of the product. Referring to FIGS. 18 and 19, the multi-layer construction is rolled and sealed to itself along seal edge 555 by either a butt or lap seam or other methods as known in the art. This tubular shape can then be bonded on both open ends along seal edge 550 as shown in FIG. 18 so as to contain the perfume on the inside. In doing so the shade is sealed on all sides to prevent perfume loss and the shade becomes the primary package. Sealed ends 550 of shade/package 570 can then be removed by the user in any number of ways known to those of ordinary skill in the art including but not limited to cutting them off with a scissors or utilizing perforations 540 such as shown in FIG. 17, peel tape, pull strips, or any other convenient easy means of opening barrier pouches. The shade/package 570 can then be placed into an open configuration by the user one non-limiting example of which is the cube form shown in FIG. 19. Once in the open configuration, perfume can then be released from the inside of the shade/package. Optionally, an element 560 can be used to retain the shape of the folded cube to keep it in the open cube form. Non-limiting examples of such element 560 would be a piece of aluminum foil tape or a tin tie as shown in FIG. 18. A further option (not shown) could be a frame which would fit around the top of the cube form so as to help retain the shape of the cube.

When the inner absorbent layer is comprised of PET or other synthetic fibers that are difficult to tear it may be desirable to have the inner absorbent layer not extend to the barrier layer thus preventing the inner absorbent layer from being in the sealed end portion of the shade/package. It may be desirable for the integrated shade/package to be comprised of a transparent barrier layer, non-limiting examples of which are EVOH and/or silicon dioxide so as to allow light to pass through the luminary shade.

In another non-limiting embodiment, the shade may include multiple components such as an inner and outer shade both of which can be of similar shape and size or could be a different size and/or shape from one another. If desired, the outer or inner shade or both could either be scented, unscented, or one or the other scented. A non-limiting example of this is shown in FIGS. 13-15. Referring to FIGS. 13 and 15, the outer shade 410 could be an unscented decorative shade while inner shade 440 could be scented. Inner shade 440 could be a similar shape but slightly smaller than outer shade 410 so that inner shade 440 could be easily inserted on base 20 and/or cover 22 without interfering with outer shade 410. Referring to FIG. 15, (a cross-sectional view taken along lines 13-13 of FIG. 13) outer shade 410 and inner shade 440 are shown resting on base 20 and cover 22. Base 20 can optionally include a ledge 293 so as to help facilitate the centering of inner shade 440 within outer shade 410. Outer shade 410 could be made of a similar material as inner shade 440 or alternatively outer shade 410 could be made from a more decorative and/or more expensive material. Inner shade 440 if desired could be a simpler form than outer shade 410 and could for example include a fragrance thereby allowing inner shade 440 to be changed more frequently while outer shade 410 is used for repeated uses. Outer shade 410 could be used once, several times, or could be a durable shade meant to be used as a decorative element for many uses. If desired, outer shade 410 could be durable or semi-durable while inner shade 440 could be disposable. Alternatively, outer shade 410 could be disposable while inner shade 440 is durable or semi-durable. Yet further, if desired, both outer shade 410 and inner shade 440 could be durable or semi-durable or both outer shade 410 and inner shade 440 could be disposable. A more durable outer shade 410 could be made from a durable translucent material non-limiting examples of which include glass; plastics such as polycarbonate, CPET, polypropylene, or other plastics that can preferably be injection molded; vellum; cellulosic materials such as specialty papers; or various woven and non-woven materials. A durable shade could also be made from a material that is not translucent and has openings to allow for light to pass through. Non-limiting examples of materials which could compose non-translucent durable sheets include thick/high caliper paper structures, metal, colored plastic materials, or combinations thereof. Utilizing separate inner and outer shades allows for more decorative materials to be utilized for the outer shade without limitations related to cost, perfume compatibility, and ink compatibility. Furthermore, utilizing a separate outer and inner shade allows a user to mix and match decorative shades with different scented shades. This could also potentially reduce the number of variations that a store would need to maintain in stock.

Figure 16A:
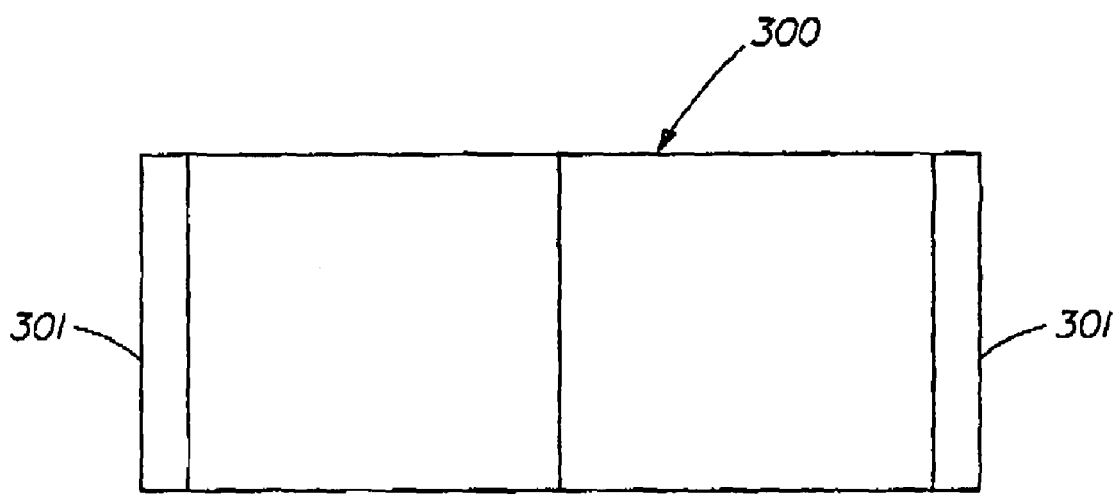
FIG. 16A is a front view of an embodiment of a shade made in accordance with the present invention.
Figure 16B:
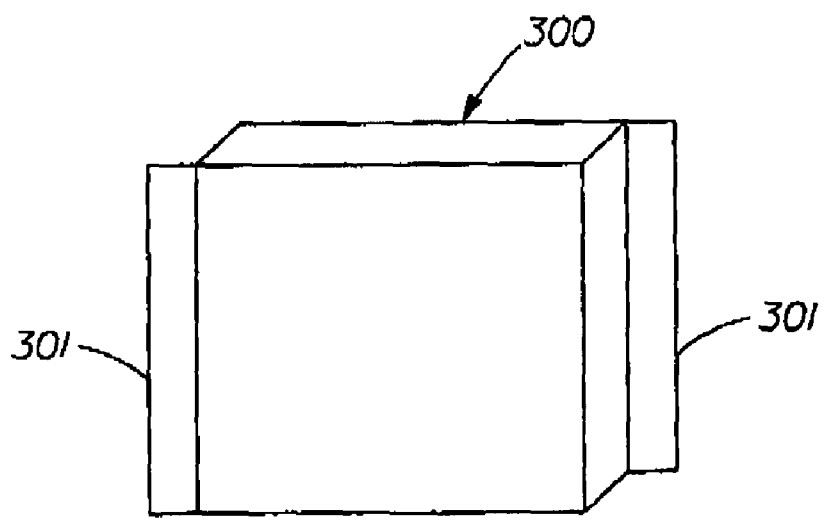
FIG. 16B is a top perspective view of the shade of FIG. 16A.

If desired, a scented shade 300 could be constructed to have one or more handles a non-limiting example of which are tabs 301 as shown in FIGS. 16A and 16B so as to allow a user to handle shade 300 without potentially getting perfume on their hands. Tabs 301 also provide an easy way to grab shade 300 by squeezing tabs 301 inward so as to allow shade 300 to form a shape such as the cube shape shown in FIG. 16B. Tabs 301 could also if desired form the seal area where layers forming shade 300 are combined such as by adhesively combining, heat sealing, or the like.

D. Volatile Composition

The decorative luminary 10 of the present invention may also comprise a volatile composition. As used herein, the terms "scent", "fragrance", "aroma", and "perfume" are used interchangeably. The volatile composition of the present invention can encompass volatile materials including but not limited to volatile dyes, fragrance compositions, compositions that function as insecticides, air fresheners, deodorants, aromacology, aromatherapy, essential oils, or any other material that acts to condition, modify, or otherwise emit into the atmosphere or to modify the environment. Deodorants or malodor control compositions may comprise a material chosen from: odor neutralizing materials a non-limiting example of which is reactive aldehydes (as disclosed in U.S. published application No. US 2005/0124512), odor blocking materials, odor masking materials, or sensory modifying materials, a non-limiting example of which is ionones (as disclosed in US 2005/0124512), and combinations thereof.

Typically the volatile composition is contained within the shade 40 and/or the base 20. The volatile composition may also be included in a separate sachet or pouch (not shown). As used herein, the terms "sachet" and "pouch" are used interchangeably. Generally, the volatile composition that is included in the shade 40, the base 20, separate sachet or the like, or a combination thereof, is included in an amount of about 60 milligrams to about 15 grams per shade, base, separate sachet or combination thereof; or from about 120 milligrams to about 5 grams per shade 40, base 20, separate sachet or combination thereof, or from about 250 milligrams to about 1 gram per shade 40, base 20, separate sachet or combination thereof. In one non-limiting embodiment the shade 40 is impregnated with about 0.1 gram to about 2 grams of the volatile composition or from about 0.3 grams to about 0.8 grams of the volatile composition. In one non-limiting embodiment, the volatile composition after exposure to air is about 50% or more depleted from the shade 40, the base 20, sachet, etc., within about twenty-four hours, or within about twelve hours, or within about six hours assuming an approximate temperature of 21° C. and an approximate 50% relative humidity of the air in the location where the volatile composition is located.

In one embodiment, the volatile composition could comprise a perfume composition. The perfume composition can provide a short-term scent experience. A number of methods to control the intensity of scent within the present invention are envisioned. In some cases, this can be a product of the perfume composition, or the design of the shade 40, base 20, or any surface to which the perfume composition is added, or a combination thereof. For example, the perfume composition can be formulated so that it has characteristics that provide it with a more rapid release profile. Perfumes typically comprise one or more perfume ingredients. Often, these ingredients have different volatilities, boiling points, and odor detection thresholds. When a perfume composition volatilizes into the air, the ingredients with the higher volatilities (referred to as "top notes") will be the ingredients that will volatilize and be detected by a person's sense of smell more quickly than the ingredients with lower volatilities (referred to as "middle notes") and the ingredients with the lowest volatility (referred to as "bottom notes"). This will cause the character of the perfume to change over time since after the perfume is first emitted, the overall perfume character will contain fewer and fewer top notes and more bottom notes.

The perfume compositions can include components that are suitably used in volatile composition emitting devices such as the present invention. The components are not limited but can be selected based on their Kovat's Index ("KI") (as determined on 5% phenyl-methylpolysiloxane as non-polar silicone stationary phase). The KI places the volatility attributes of an analyte (e.g. component of a volatile composition) on a gas chromatography column in relation to the volatility characteristics of an n-alkane (normal alkane) series on that column. A typical gas chromatograph ("GC") column is a DB-5 column available from Agilent Technologies of Palo Alto, Calif. By this definition, the KI of a normal alkane is set to 100n, where n is the number of carbon atoms in the n-alkane. The KI of an analyte, x, eluting at time t', between two n-alkanes with number of carbon atoms "n" and "N" having corrected retention times $t'_n$ and $t'_N$ respectively, will then be calculated as:

$$KI = 100\left(n + \frac{\log t'_x - \log t'_n}{\log t'_N - \log t'_n}\right)$$

On a non-polar to slightly polar GC stationary phase, KI of analytes are correlated with their relative volatility. For example, analytes with smaller KIs tend to be more volatile than those with larger KIs. Ranking analytes with their corresponding KI values gives a good comparison of analyte evaporation rates in liquid-gas partitioning systems. The volatile composition according to the present invention can have at least one ingredient with a KI value of about 600 to about 1800, or about 800 to about 1700, or about 900 to about 1600. The volatile composition can comprise about 50% to about 100%, or about 70% to about 100%, or about 80% to about 100% of one or more ingredients having these KI values.

Rather than, or in addition to Kovat's Index, the volatile composition components can be selected based on their boiling point (or "B.P.") and their octanol/water partition coefficient (or "P"). The boiling point referred to herein is measured under normal standard pressure of 760 mm Hg. The boiling points of many perfume ingredients, at standard 760 mm Hg can be found in "*Perfume and Flavor Chemicals (Aroma Chemicals)*," written and published by Steffen Arctander, 1969.

The octanol/water partition coefficient of a perfume ingredient is the ratio between its equilibrium concentrations in octanol and in water. The partition coefficients of the perfume ingredients used in the volatile composition may be more conveniently given in the form of their logarithm to the base 10, logP. The logP values of many perfume ingredients have been reported; see for example, the Pomona92 database, available from Daylight Chemical Information Systems, Inc. (Daylight CIS) of Irvine, Calif. However, the logP values are most conveniently calculated by the "CLOGP" program, also available from Daylight CIS. This program also lists experimental logP values when they are available in the Pomona92 database. The calculated logP ("ClogP") is determined by the fragment approach of Hansch and Leo (A. Leo, in Comprehensive Medicinal Chemistry, Vol. 4, C. Hansch, P. G. Sammens, J. B. Taylor and C. A. Ramsden, Eds., page 295, Pergamon Press, 1990). The fragment approach is based on the chemical structure of each perfume ingredient, and takes into account the numbers and types of atoms, the atom connectivity, and chemical bonding. The ClogP values, which are the most reliable and widely used estimates for this physicochemical property, are typically used instead of the experimental logP values in the selection of perfume ingredients for the volatile composition.

The perfume composition might comprise perfume ingredients selected from one or more groups of ingredients. A first group of ingredients may comprise perfume ingredients that have a boiling point of about 20° C. to about 250° C., or a boiling point of about 25° C. to about 240° C., or a boiling point of about 30° C. to about 235° C. The first group of ingredients may comprise perfume ingredients that have a ClogP value from about −2 to about 3 or from about −1 to about 2.5. In certain embodiments, perfume ingredients selected from the first group of perfume ingredients when present may be present at a level of from about 20% to about 100% by weight of the perfume composition, or from about 40% to about 100% by weight of the perfume composition, or from about 50% to about 100% by weight of the perfume composition.

A second group of ingredients might comprise perfume ingredients that have a boiling point of about 20° C. to about 250° C., or a boiling point of about 25° C. to about 240° C., or a boiling point of about 30° C. to about 235° C. The second group of ingredients may comprise perfume ingredients that have a ClogP value from about 3 to about 9 or from about more or about 3.5 to about 7. In certain embodiments, the second perfume ingredient when present may be present at a level of from about 20% to about 100% by weight of the perfume composition, or from about 40% to about 100% by weight of the perfume composition, or from about 50% to about 100% by weight of the perfume composition.

A third group of ingredients might comprise perfume ingredients that have a boiling point of about 250° C. to about 400° C., or about 260° C. to abut 375° C. The third group of ingredients may comprise perfume ingredients that have a ClogP value of about from about −2 to about 3 or from about −1 to about 2.5. In certain embodiments, perfume ingredients selected from the third group of perfume ingredients when present may be present at a level of about 0.5% to about 90% by weight of the perfume composition or about 1% to about 80% by weight of the perfume composition.

A fourth group of ingredients might comprise perfume ingredients that have a boiling point of about 250° C. to about 400° C., or about 260° C. to abut 375° C. The fourth group of ingredients may comprise perfume ingredients that have a ClogP value from about 3 to about 9 or from about more or about 3.5 to about 7. In certain embodiments, perfume ingredients selected from the fourth group of perfume ingredients when present may be present at a level of about 0.5% to about 90% by weight of the perfume composition or about 1% to about 80% by weight of the perfume composition.

When formulating perfume compositions, some perfume ingredients may also have other functionality such as functioning as a solvent, diluent, extender, fixative, or the like. Non-limiting examples of these materials are ethyl alcohol, carbitol, diethylene glycol, dipropylene glycol, diethyl phthalate, triethyl citrate, isopropyl myristate, and benzyl benzoate.

In addition to methods described above for delivering the volatile compositions of the present invention, other non-limiting suitable methods for delivering these compositions are discussed below. In one non-limiting embodiment a volatile composition may be delivered by utilizing a pouch with a semi-permeable membrane on at least one side of the pouch. The pouch may be attached to the shade 40. The membrane may be selected from several known materials which can allow perfume vapor to pass without allowing significant liquid leakage. Examples of suitable membrane materials include but are not limited to polyethylene and microporous polyethylene, ethylene vinyl acetate, microporous polytetra-flouralethylene ("PTFE"), and other microporous membranes as known in the art. These membranes allow volatile actives to be released by either rapid diffusion through the membrane material such as with a thin polyethylene film or by evaporation through porous regions of the material such as microporous PTFE.

The scent intensity of the shade 40 can optionally be varied by varying the size of the shade 40 in width and/or height as well as by changing the pore size of the material and/or the material properties. Shades 40 at different heights yet same width can be provided to deliver different levels of scent intensity as well as to effectively communicate to the end user which shade 40 to use for the room or occasion. For example, a scented shade 40 of the present invention with a 20 cm circumference and 22 cm height may be an appropriate size for a living room or family room and a scented shade 40 with a 20 cm circumference and a 10 cm height may be a size appropriate for a bathroom or smaller space. Typically the shades 40 are of a similar circumference such that the shade 40 will fit over the same base.

The release rate of the volatile composition from a substrate could also be controlled by providing layers wherein the release rate can be customized to last different periods of time. For instance, the substrate could include one or more layers. An individual layer could be an intermittent or continuous layer that is designed to release the perfume at various time intervals. The layer can be activated with UV light, oxygen, moisture change, or other stimuli.

In another non-limiting embodiment, the release of the volatile composition could be changed by varying the material properties of the shade 40. While not wishing to be limited by theory, in general, volatile compositions impregnated in a polymer such as a thermoplastic will release slower than volatile compositions loaded in an absorbent or porous material. Porous materials exposed to the atmosphere will allow volatile compositions to evaporate at the surface whereas volatile compositions impregnated in a polymer generally require the volatile composition to diffuse through the polymer. For example, a thermoplastic material such as an EVA or polyolyefin can be impregnated with a perfume and the diffusion properties and/or thickness of the thermoplastic can be tailored to release the perfume at varying rates. Incorporating open or closed cells in the thermoplastic will also have a big effect on the diffusion properties and these cells can change the effective level of perfume that is saturated or absorbed into the material. While not wishing to be limited by theory, in general, open cells/pores will release volatile compositions faster than closed cells since the open cells allow for the volatile composition to be exposed directly to the atmosphere to evaporate and therefore minimizes the need for diffusion of the composition through the cell walls. It is known in the art that various foaming agents and/or gases can be incorporated in the process of extruding or injecting the thermoplastic to create these pores or cells in the plastic wall. Engelhard Corporation of Iselin, N.J. is one suitable manufacturer of foaming agents that can be incorporated in thermoplastic extrusion processes. Trexel Incorporated of Woburn, Mass. is a provider of technology for injecting gases in thermoplastic create closed cell foam-like materials suitable for use with the present invention. Non-limiting examples of open celled thermoplastic foams suitable for use with the present invention are CELLECT foams available from Sentinel Products Corporation of Hyannis, Mass.

Another means of controlling the release of the volatile composition is by encapsulating the volatile composition in the form of capsules non-limiting examples of which include microcapsules, or starch encapsulates. There are a number of means in which the capsules can be designed to release the scent. For example the scent can be released by either rupturing the capsules or by diffusion through the capsule wall. In another example the scent is released from the microcapsule when moisture in the air causes the capsule wall to rupture. Alternatively, the capsules can be ruptured by peeling off an adhesive layer that causes the microcapsule to tear or rupture. The capsule size and material properties can also be adjusted to control the diffusion.

In another non-limiting embodiment, when the perfume is located inside of the shade 40, the release of the perfume could be controlled by varying the air flow through the inside of the shade 40 so as to change the evaporation rate of the perfume. While not wishing to be limited by theory, this could be thought of as a chimney effect except that the vapors from the perfume may flow upward or downward depending upon the perfume and the shade design. It is believed that the perfume will naturally cool the air when it evaporates and hence the air flow is naturally downward due to the cooler air being heavier. Typically most perfumes are naturally heavier than air and hence there is a tendency for the perfume to "sink" or flow downward. To maximize scent release, it is desirable that the shade 40 be fully open on the top and bottom to maximize air flow.

Figure 12:
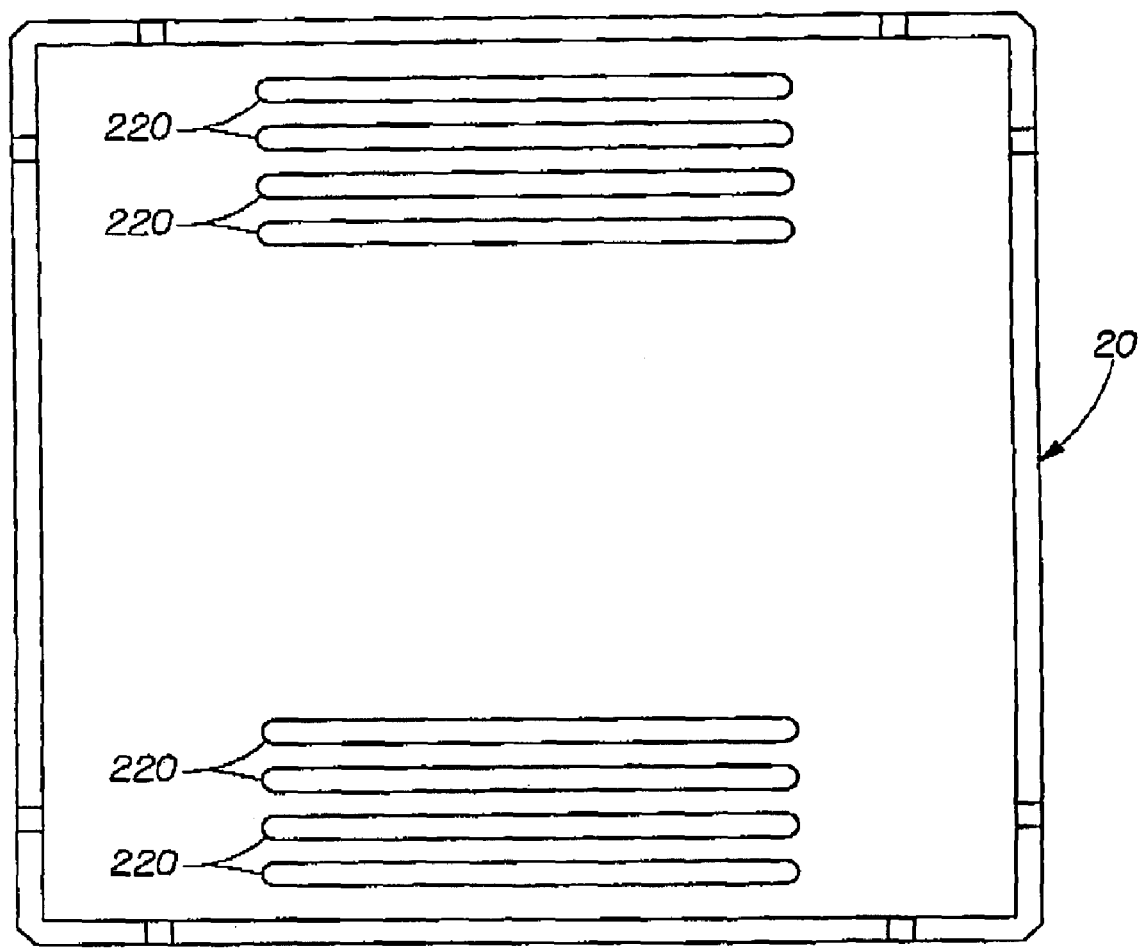
FIG. 12 is the bottom view of the decorative luminary of FIG. 11.

Furthermore, the larger the shade 40 opening is on the top and the bottom, the more the air flow will be through this opening. This can be especially desirable with perfumes which comprise higher molecular weights or higher KI values which tend to have slower evaporation rates. To minimize or stop scent release, it is desirable that the top and bottom openings of the shade 40 be substantially closed from the environment. For instance, the top and/or bottom of the shade 40 could have vents 220 such as those shown in FIG. 10. Additionally, or alternatively, referring to FIGS. 11 and 12, the base 20 could also include vents 220. If desired the vents could be designed such that they that can be closed or opened (to some degree) to regulate/adjust the perfume evaporation rate. There are a number of non-limiting ways in which the top of the shade 40 and/or the base 20 could be made to adjust air flow. For instance, in one non-limiting example, an adjustable slide (not shown) could be included in the bottom of the base 20 which would allow a user to rotate or slide an element that opens or closes the openings that allow air flow through the inside of the shade 40. In another non-limiting example, the top of the shade 40 could be adjusted to control air flow through the top. One non-limiting example is to use a frame (not shown) that fits on top of the shade 40 and has an integral slide element that can be rotated or slid open to open or close the top vent. Another non-limiting means of doing this would be to utilize a material which upon folding retains the folded shape. For instance, the top of the shade 40 could be comprised of a material such as a thin metal which upon applying pressure to both sides of the top of the shade 40, the two sides would come together so as to close the opening thereby limiting air flow through the shade 40 opening. In another non-limiting example, the top opening of the shade 40 could be restricted by using a draw string, a thin metal wire tie, or the like.

In another non-limiting embodiment for controlling the evaporation rate of the perfume, a small amount of heat could be used to help drive air flow. While not wishing to be limited by theory, it is believed that a temperature rise of about 0.2° C. to about 1° C. combined with appropriate venting can potentially result in higher air flow through the inside of the shade 40. This chimney effect with a small temperature rise can be obtained in a number of different ways including but not limited to via the heat output of lights, circuitry, a small heater such as a battery powered heater, or via heat producing reactive chemistries that can be incorporated in the shade 40 and/or the base 20 such as iron oxide. In one non-limiting method, iron oxide particles can be coated or encapsulated with a fragrance and applied to shade 40. Shade 40 could then be placed in a nitrogen flushed foil pouch that will prevent the oxidation of the iron oxide until the pouch is opened. The nitrogen flushed pouch can also be used to prevent oxygen from oxidizing the fragrance as well as prevents the fragrance from evaporating prior to use by the consumer. When the pouch is opened by the user the iron oxide encapsulated with perfume begins to heat up and results in a higher evaporation rate of perfume. This will allow low volatility perfumes to be more easily dispersed in a room providing superior scent quality with an evaporative scent release system.

The shade 40 could have multiple scents and/or scents that release at different time intervals. In some instances it may be desirable for a particular scent to be released for the first 4 hours and a different scent begins to be released for the next 4 hours. This can be done by treating one side of the shade 40 with one technology as described above and a different technology (e.g.; different material, coating, thickness, or other) could be used on the other side. This provides the benefit of either extending the scent over a longer period of time or providing alternating scents so as to help reduce acclimation to the scent by the user.

The shade 40 could also be dosed or refilled with a volatile composition including but not limited to a perfume by the user using ampoules, pouches, dropper bottle, sachets, a spray, or any other means of delivering a fluid to the shade 40. A non-limiting example would be the use of individually contained pouches containing about 0.5 ml to about 5 ml of a perfume composition that a user could apply by tearing off a corner of a pouch and squeezing the contents onto the shade 40. In another non-limiting example, about 0.5 ml to about 5 ml of perfume could be contained in either a small individual or multi-use unit dosed blow-fill seal container similar to those unit dose containers used as contact eye solution containers. One suitable manufacturer of equipment to make such unit dose packages is Rommelag USA Incorporated of Edison, N.J. Alternatively, the perfume could be encapsulated and loaded onto the shade 40 and an occasional spray of water by the user could be used to release the volatile composition.

In another non-limiting embodiment, it may be desirable to treat the outside of shade 40 with a deodorizing ingredient. Non-limiting examples of such ingredients would include titanium dioxide, cyclodextrin, metal oxides, polyoxometalates, and the like. While not wishing to be limited by theory, it is believed that having deodorizing ingredients on the inside or outside of shade 40 would provide a means for delivering odor elimination benefits beyond masking the odors with fragrance or using reactive fragrance ingredients such as reactive aldehydes as mentioned previously. It is believed that the deodorizing ingredients are ideally placed in a position where air flow moves across the deodorizing ingredients prior to the air evaporating the perfume. In this way the deodorizing ingredients are not removing the perfume from the air. Non-limiting examples of locations could include along the edge of shade 40 where air flows into the shade.

E. Optional Additional Components

The present invention may also include other optional components, a non-limiting example of which is a signal that communicates the status of the decorative luminary 10 to a user. For example, there may be a signal which indicates when the process has commenced and/or concluded. Non-limiting examples of signals which may be used include color, sound, and/or olfactory signals.

In some instances it may be desirable that the light source recognize the shade 40 so as to adjust the light pattern, intensity, or duration based on the age of the shade 40, design of the shade 40, scent type, and/or intensity of the scent release. This would allow for a smart device that could deliver superior light 27, scent, and/or a dynamic indicia pattern experience (i.e.; where the indicia appearance changes during use). Alternatively, this could also be used to recognize when a shade is depleted of its scent and ready for replacement.

One non-limiting means by which this can be done is to incorporate a small microchip such as a Radio Frequency Identification ("RFID") chip) that communicates with the base 20. For example, an RFID chip could be incorporated into the shade 40 while an RFID sensor capable of detecting the RFID chip could be incorporated into the base 20. In one non-limiting example, the RFID sensor could detect whether the shade 40 is present by detecting the RFID chip in the shade 40 in order to send a signal to turn the light 27 on or in another non-limiting example the RFID sensor could detect whether the shade 40 with the RFID chip has been depleted of volatile composition. RFID chips and sensors suitable for use with the present invention are available from Texas Instruments of Dallas, Tex.

Another means to accomplish this would be to provide a color coded region on the shade 40 that is detected by a light sensor such as a photo-eye located within the base 20. One non-limiting example of this is where the shade 40 would have a particular color in a given region that could be detected by the photo eye in the base 20 which in turn could activate a light 27 upon sensing this color. This color coded region can also be designed to change color with time so as to communicate with the base 20 as to the age of the shade 40 and/or communicate when the shade 40 needs to be replaced.

Optionally, the shade 40 may function in combination with the base 20 to provide a time indicator. For instance, the time indicator could provide a signal that the scent of the shade 40 is depleted. For example, the light 27 could be made to dim or not function after the shade 40 has been used for a period of time. One non-limiting means of accomplishing this is to incorporate a surface mounted fuse such as those manufactured by Littelfuse Corporation of Des Plaines, Ill. into the shade 40 so that it is in electrical contact with the control circuitry of the light source. In this case, an electrical spike from the light source microcontroller could cause the fuse to open after a set time period corresponding to the scent duration. If the base 20 senses an open fuse on the shade 40, the light will not function or will dim. Another approach is to have a wet region of the shade 40 or a region of the shade 40 that contains an electrolyte such that electricity is conducted through this region when wet and no electricity is conducted when the region is dry. This in turn can be used as a communication signal to the light source that the shade 40 is fully used and needs to be replaced. Another approach is to incorporate a thin electrically conducting metal in the bottom portion of the shade 40. While not wishing to be bound by theory, it is believed that the resistance of the metal will increase over time. The light source would then measure the resistance and based on this would be able to determine the age of the shade 40.

In another non-limiting example the shade 40 may include a color changing dye. The color changing dye could be detected by a light sensor such as a photo-eye located within the light base. For instance, when the shade 40 is activated, for example by a user opening the package containing the shade, a color change on the bottom of the shade 40 begins to occur. The color change could occur for example as a result of utilizing an oxidative ink and/or an ink that reacts with carbon dioxide present in the air. This color change can be designed to take a number of hours or days and can be used to communicate with the light base to send a signal as to whether this is a new shade or an old shade that needs to be replaced. The color change can also potentially communicate the scent and desired intensity and adjust the light to vary the intensity, duration, or flickering pattern of the light. The color change could correspond to a predetermined code for the shade 40 such that the base would know what type of shade 40 is present. For instance a black dot could be associated with one scent experience while a blue dot could be associated with a different scent experience.

These fuses and/or circuit connectors within the shade 40 have the added benefit of also preventing the base 20 from working properly unless a new shade of the right design is placed on the base 20. In yet another non-limiting example, the shade 40 and/or the base 20 may include indicia. The indicia may be static or it may be dynamic. In one non-limiting example, the base 20 could include an extended region/sleeve that includes indicia. The indicia could be visible or non-visible through the use of light. Non-limiting examples of which include light provided by the use of flat panel displays or fiber optics. The indicia may be in the form of a decorative pattern or image to provide an aesthetically pleasing article. In addition to or alternatively, the indicia can be used to provide a signal to a user such as when the shade 40 needs to be changed and/or when the scent is depleted. The shade 40 can be printed with inks that are stable (i.e.; inks that do not bleed, dissolve, or rub-off easily) while in contact with a perfume or oil. In one non-limiting example, the indicia may be printed by utilizing an inkjet printer. One non-limiting example of a suitable inkjet printer is a DESKJET 950C inkjet printer equipped with ink cartridges Part Nos. 51645A and C6578D, available from Hewlett Packard Corporation of Palo Alto, Calif. The indica can also be printed by any other known printing method including but not limited to flexographic printing, screen printing, gravure, offset printing, air knife, roll coating, blade coating, and the like.

The shade 40 may include indicia that undergo a visual change following activation by the user. In one non-limiting example the shade 40 is imprinted with indicia that undergo a visual change following activation by the user. Alternatively or in addition to the above, the entire shade 40, or some portion of the shade 40 may undergo a visual change including but not limited to an opacity change following activation. Activation may include, for example, removal of the shade 20 from a secondary package, rupturing of a pouch, removal of a film, addition of a film, addition of a liquid, or other action that results in a stimuli to affect the visual change. Possible stimuli include changes in oxygen, carbon dioxide, or humidity of the surrounding atmosphere, changes in the amount of some other vapor in the surrounding atmosphere, changes in pH or temperature, exposure to ultraviolet or infrared radiation, or some other stimuli. The visual change may be in the form of a decorative pattern that appears, disappears, changes color, changes intensity, changes opacity, or any combination of these effects. The visual change will generally occur during the first 8 hours after activation, or during the first 4 hours after activation, or during the first 2 hours after activation.

The visual change may be triggered by a variety of means. For example, the decorative pattern may appear, disappear, or change color as a result of a change in the air composition (i.e.; oxygen, carbon dioxide, nitrogen, and the like) of the atmosphere surrounding the shade. In one non-limiting embodiment, an oxygen indicator may be used, wherein the shade is printed with an oxygen indicator and is placed in a high barrier (e.g.; metalized PET or foil) pouch that is flushed with nitrogen or a different inert gas and then sealed to prevent oxygen from entering the pouch. Upon activation, e.g.; removal from the pouch, a color change would occur as exposure to oxygen in the atmosphere triggers the oxidation of the indicators. Suitable oxygen indicators and methods of preparing oxygen indicators are disclosed, for example, in U.S. Pat. Nos. 4,349,509, 4,526,752, 4,812,053, and 6,703,245. Alternatively, another non-limiting example would be the visual change which may be triggered by a change in the concentration of carbon dioxide in the air in the presence of the shade 40.

The decorative pattern may appear, disappear, or change color for example as a result of a change in pH. Suitable indicators that change color with a change in pH include but are not limited to: phenolphthalein, thymolphthalein, m-Nitrophenol, ethyl red, and Congo red just to name a few. These acid base indicators can be found in the CRC Handbook 60th Edition published in 1979 on pages D150-D153. Other widely know indicators include fluorescent indicators such as salicylic acid, acridine, and others as described in the CRC Handbook. Alternatively a volatile acid or base could be incorporated into the shade and kept stable with either barrier peelable layers or high barrier packaging that completely surrounds the shades and prevents the volatile components from evaporating or moving. Upon peeling of a layer or opening of a barrier package the volatile components are allowed to evaporate causing a pH change and hence a color change on the shade 40 where these components are present. In one non-limiting example, the pH change may result from a change in carbon dioxide content of the atmosphere surrounding the shade 40. For example, the shade 40 may be packaged in a barrier package substantially impermeable to carbon dioxide under an atmosphere richer or poorer in carbon dioxide than the general atmosphere.

The decorative pattern may appear, disappear, or change color or intensity as a result of capillary/wicking action. This may be accomplished in one non-limiting embodiment by providing a source of fluid contained in a discrete pouch or reservoir attached to the shade 40. Upon rupture of the discrete pouch, the fluid may wick through the shade 40 as a result of capillary action. A water activated dye or pH activated dye can be printed on the shade 40 such that it is invisible when dry but appears when wet. Alternatively the fluid may contain a dye, a pH changing ingredient that would change the pH of the fluid, a volatile composition including but not limited to perfume, or a combination thereof. Optionally, the user of the product can add water to the shade 40 by either pouring or spraying water over the material or by adding water to a holding reservoir that comes in contact with the shade 40 to allow wicking of the fluid up the shade 40. The holding reservoir can be incorporated within the base 20, can be attached to the shade 40, can be a separate piece, or a combination thereof.

In another non-limiting embodiment, the decorative pattern may appear, disappear, or change color as a result of exposure to ultraviolet or infrared radiation. The base 20 may include for example a source of ultraviolet or infrared radiation to affect the change. For example, the base 20 may include light 27 such as one or more LEDs that emits light at wavelengths below about 410 nm. An example of a suitable LED is Part No. SSL-LX5093SUVC available from Lumex Incorporated of Palatine, Ill. In conjunction with the ultravoiolet or infrared LED containing light source, the shade 40 may include indicia containing photochromic dyes such as those known in the art. Non-limiting examples of suitable photochromic dyes are those provided by Chromatic Technologies Incorporated of Colorado Springs, Colo. and available under the tradename DYNACOLOR PHOTOCHROMIC INK. The ultraviolet or infrared LED is positioned to affect a visual change in the indicia printed with the photochromic ink. The decorative pattern may disappear, or change color or intensity as a result of evaporation of a volatile dye. Non-limiting examples of suitable volatile dyes include guaiazulene (1,4-dimethyl-7-(1-methyletheylazulene, CAS# 489-84-9) and azulene (Bicyclo[5.3.0]decapentaene, CAS#275-51-4). The volatile dye may be dissolved in a solvent such as methanol, ethanol, acetone, isopropanol or other volatile solvent, or may be formulated into an ink by combination with other ingredients such as binders as is known in the art.

Another non-limiting means of creating a visual change is by designing the shade 40 so that at least a portion of the shade 40 undergoes an opacity change after activation. One way to affect the opacity change is by evaporation of a volatile composition from a porous material that makes up at least a portion of the shade 40. Porous shade materials suitable for use with this invention when wetted with water and/or a volatile composition such as a perfume will typically have an opacity decrease of about 5% to about 30% depending upon the thickness and type of material. For example, a polyester non-woven, one suitable non-limiting example of which is SYNERGEX 6130 available from BBA/Fiberweb, with a basis weight of about 100 grams/m$^2$ may have an opacity of about 63% when dry but drops to about 43% when wetted with a volatile fragrance. As the fragrance evaporates over approximately a 1 hour time period the opacity can change from about 43% slowly back to about the original 63%. This change in opacity also will effect how light from the light source is diffused and hence can be used to provide a visual signal to a consumer that the shade 40 is changing. In another non-limiting example a KIM WIPES® tissue, manufactured by Kimberly Clark Corporation of Neenah, Wis., may have an opacity of about 48% when dry and an opacity of about 25% when wetted with a liquid volatile composition such as a perfume.

If the opacity change is large enough, the changing opacity of the shade 40 can also be used to expose or hide a graphic that is printed on the shade 40. For example materials which include micropores having a mean pore size typically between about 0.01 microns and about 15 microns are opaque when dry but become semi-transparent when wetted with a fluid. Suitable materials for this purpose include but are not limited to microporous polyethylene, polypropylene, nitrocellulose, and polyester, having a pore volume of about 50% volume of pores/volume of total material ("v/v") to about 99% v/v. Examples of suitable materials include those available under the tradename SOLUPOR, grades 7P03A, 5P09B, and 10P05A available from DSM Solutech of Heerlen, Netherlands. In one non-limiting example, these microporous materials can have an opacity decrease of about 20% to about 70% depending upon the thickness, material type, and pore size. For instance, SOLUPOR 7P03A with a nominal basis weight of about 7 g/m$^2$ has an opacity of about 95% when dry and about 45% when wetted. A graphic or image can be printed on one side of the sheet and as the fluid evaporates the sheet slowly becomes opaque and eventually will let little or no light through. Initially the graphic can be seen from the other side especially with a back-light such as from a light source. As the shade dries it become more opaque letting less light pass through the shade 40 as well as making the graphic no longer visible.

The pore size of the shade material is typically between about 0.01 microns and about 50 microns or between about 0.05 microns and about 5 microns to provide the highest opacity when dry while still providing transparency when wetted. The average pore size diameter to absorb the volatile composition is typically between about 0.1 micron to about 100 microns or between about 1 micron to about 50 microns average pore size diameter. Hence, an average pore size diameter for a material that is both opaque and absorbent without the use of pigments could be between about 0.1 micron and about 50 microns. This allows for a single material to be able to hold a fluid such as a perfume and provide a semi-opaque shade when dry and semi-transparent shade when wetted with a liquid composition. Alternatively a multi-layer structure could be used for the shade whereby one layer serves as an opaque changing layer with a pore size between about 0.01 microns and about 50 microns and an additional layer is designed to hold onto a volatile composition with an average pore size between about 0.1 micron and about 100 microns.

In another non-limiting embodiment it may be desirable to have the shade 40 with a unique geometry/shape that corresponds to a similar/reciprocal geometry in the base 20 so as to ensure proper alignment and/or recognition between the base 20 and the shade 40. Suitable non-limiting examples include a tab located on the shade 40 with a corresponding indentation on the base to accommodate the tab. Another non-limiting example could be a pin/hole configuration.

Kit

The components of the decorative luminary of the present invention including but not limited to the shade 40, the base 20, the light source/light 27, the sealed pouch to hold shade 40, and the volatile composition, may be provided as a kit. Alternatively, one or more of the components of the decorative luminary may be provided separately. For instance, in one non-limiting embodiment the shade 40 of the decorative luminary may be provided with one or more of the other components as part of a kit or may be provided and/or sold separately. In another non-limiting example, the volatile composition may be provided as part of a kit, for instance it may be incorporated into the shade or provided in a separate sachet, pouch, ampoule, bottle, or the like. In yet another non-limiting embodiment, the volatile composition may be provided separately such as part of a dosing container or refill unit which may be purchased separately by a user. In an additional non-limiting embodiment, the base and/or the light source may be provided in conjunction with the other components of the decorative luminary, may each be provided as one unit, or may each be provided and/or sold separately. For instance, it may be desirable for a user to have a choice of the type of light source that is to be used or to have the flexibility to interchange the light(s) and/or the base.

It may also be desirable for a user to have the ability to choose the individual components comprising the decorative luminary 10 so as to customize the decorative luminary 10 in accordance with the individual's preferences. For instance, an interactive sample display could be provided to allow the user to choose/customize the components (e.g.; shade 40, base 20, light source/light 27, volatile composition) that he or she would want the decorative luminary 10 to be comprised of. The interactive sample display could be manually controlled by the user, computer controlled by the user, or a combination thereof. This interactive sample display could be provided electronically for instance through an internet/virtual web site or it could be located at a physical site such as at a store location, or delivered to the user's home such as through the parcel post and/or via a newspaper/magazine insert. In one non-limiting example of a manual interactive sample display, each option of each decorative luminary component is provided on a moveable wheel located along a single row of the sample display so as to overlay one component on top of the next such that the user can view what the decorative luminary 10 would look like based on the options chosen for each component. As an alternative or in addition to the above, different samples of the volatile composition, for instance a perfume, could also be overlaid with the components for example in a scratch and sniff type of configuration so that the user can have the benefit of holistically customizing/choosing the decorative luminary 10 which best meets the user's individual preferences prior to making a final purchase commitment.

Self-Instructing Article of Commerce

The present invention also encompasses articles of commerce comprising 1) the decorative luminary 10 of the present invention, and 2) a set of instructions directing the user how to utilize the decorative luminary 10.

In one embodiment, the article of commerce comprises the decorative luminary 10 of the present invention in association with a set of instructions, wherein the instructions direct the user to follow the method of utilizing the decorative luminary 10. The instructions may be in the form of written words, pictorials, symbols/icons, and the like, as well as combinations thereof. In one embodiment, such instructions would direct the user to 1) place the decorative luminary 10 on a surface; and 2) activate the decorative luminary 10 for instance by removing the shade 40 from the package and/or by placing it in the base 20.

Herein, "in association with", when referring to such instructions, means the instructions are either directly printed on the decorative luminary 10; directly printed on the packaging for the decorative luminary 10; printed on a label attached to the decorative luminary 10 or the packaging for the decorative luminary 10; or presented in a different manner including, but not limited to, a brochure, print advertisement, electronic advertisement, broadcast or internet advertisements, and/or other media, so as to communicate the set of instructions to a consumer of the decorative luminary.

EXAMPLES

Non-limiting examples relating to the instant invention are disclosed below.

Example 1

A wicking shade is made by incorporating a rupturing pouch in the base of the shade. The rupturing pouch is made with a high barrier metalized PET laminate manufactured by Pechiney Plastic Packaging of Neenah, Wis. with a SURLYN® sealant available from DuPont of Wilmington, Del. The pouch is sealed with a lower temperature on one side (approximately 93° C. versus approximately 149° C. for the other two sides of the pouch) to create a frangible seal that will burst with less than about 5 pounds (2.3 kilograms) of force when pressed. The pouch is filled with about 3 ml of water, 3 drops of a green food color dye, and about 1 ml of a pine scent perfume oil. The shade is constructed by taking a 6 inch×11 inch (15 cm×28 cm) piece of absorbent paper (non-limiting examples of which are paper towel, facial tissue, and bath tissue) with a basis weight of 50 g/m² and laminating it to a 1 mil (0.0254 mm) layer of polyethylene film such that one side is absorbent paper and the other side is polyethylene film. The paper side is then covered with a template in the shape of a tree and a lacquer coating is sprayed onto the paper to create porous and non-porous regions in the paper for controlled wicking of a fluid. A rupturable pouch is then placed on the paper side of the shade material and the bottom edge is folded over the pouch and sealed to prevent the pouch from coming loose and moving within the shade. The shade is then folded in the form of a tube with a 0.25 inch (6.35 mm) overlap and sealed along the 6 inch (15 cm) edge to create a tube approximately 9 inches (23 cm) tall with a circumference of 10.5 inches (27 cm) due to the overlap. The shade is folded such that the polyethylene side is on the outside of the tube and the paper is on the inside. The rupturable pouch is located at the base of the tree such that when ruptured the fluid would release near the base and slowly wick up the tree based on the capillary properties of the paper and paper/film lamination. The shade is then placed in an 8 inch×5 inch (20 cm×13 cm) foil pouch and sealed.

The consumer uses the shade by opening the foil pouch. This is done by the consumer tearing off the sealed region along one edge of the foil pouch. The shade is removed and placed over a battery powered light base. The scent/colored dye in the rupturable pouch is activated by squeezing the shade and light base in the region where the rupturable pouch is located at the bottom of the shade. In doing so the pouch is ruptured which allows for the release of approximately 3 cc to about 4 cc of fluid. This fluid then comes into contact with the shade. The outside of the shade and the bottom of the shade do not become wet as the film side of the shade keeps the bottom surface and the outside of the shade dry. In approximately 30 minutes the fluid wicks up about 2 inches (5 cm) of the shade. Within 120 minutes the fluid wicks up the full 6 inch (15 cm) height of the shade. In this particular example, a tree pattern appears as the wicking occurs since the colored dye will only wick in the porous regions of the paper. The wicking fluid also delivers scent such that there is no initial scent delivered upon bursting the pouch but rather the scent is slowly released as the scent/oil mixture in the pouch wick up the paper and evaporate.

Example 2

A shade comprising three layers, including a translucent paper sold by CTI Paper USA of Sun Prairie Wis. under the name "Parchment White Glama Natural" with a nominal basis weight of 110 g/m², a low density polyethylene film having a thickness of about 0.03 mm, and a creped tissue paper having a nominal basis weight of about 23 g/m², sold by Cellutissue Incorporated as grade 7020, are arranged so that the low density polyethylene is in between the two paper layers. The three layers are then thermally bonded using a thermal roll laminator set to sufficient temperature and laminating pressure to prevent the layers from being easily separated.

The 3-layer laminate described above is folded and cut to form a tube having a circumference of 190 mm and a height of 220 mm. The tube is formed so that the creped tissue paper is located on the inside of the cylinder. The seam of the tube is secured by applying transfer adhesive tape (sold as 9471 LE available from 3M Corporation of St. Paul, Minn.), to an approximate 0.5 inch (1.3 cm) overlap. The tube is then creased to form a flat structure.

Approximately 0.7 g of a volatile composition having the composition shown in (Table 1) (wherein greater than 90% by weight of the volatile composition's ingredients have a KI value of less than about 1500) is applied to the creped tissue paper layer of the 3-layer laminate tube using a transfer pipette. The 3-layer laminate tube is then promptly placed into a metalized poly bag (available from ULine Corporation of Waukegan, Ill. as Part No. S-6176) and heat sealed.

After approximately 16 hours the 3-layer laminate tube is removed from the metalized bag and opened into the tube shape and placed into a room having a temperature of approximately 70° F. (21° C.). After about 6 hours, about 50% of the perfume originally in the shade at the time of removal from the metalized bag is evaporated from the shade. After about 24 hours, more than about 70% w/w of the perfume originally in the shade at the time of removal from the metalized bag is evaporated from the shade.

TABLE 1

Composition of Volatile Composition of Example 2

| Material Name | Approximate KI Value | % w/w | Approximate Boiling Point (° C.) |
|---|---|---|---|
| Allyl Caproate (cas # 123-68-2) | 1083 | 3 | 190 |
| Ethyl Acetate (cas #141-78-6) | 610 | 3 | 77 |
| Benzaldehyde (cas # 100-52-7) | 971 | 2 | 179 |
| Prenyl Acetate (cas # 1191-16-8) | 919 | 8 | 152 |
| Benzyl Acetate (cas # 140-11-4) | 1173 | 15 | 214 |
| Ethyl-2-methyl Butyrate (cas # 7452-79-1) | 850 | 8 | 132 |
| Amyl Acetate (cas # 628-63-7) | 912 | 3 | 149 |
| Cis 3 Hexenyl Acetate (cas # 3681-71-8) | 1009 | 3 | 166 |

TABLE 1-continued

Composition of Volatile Composition of Example 2

| Material Name | Approximate KI Value | % w/w | Approximate Boiling Point (° C.) |
|---|---|---|---|
| Ligustral (cas # 27939-60-2) | 1094 | 5 | 177 |
| Melonal (cas # 106-72-9) | 1060 | 1 | 116 |
| Hexyl Acetate (cas # 142-92-7) | 1016 | 8 | 146 |
| Fruitate (cas # 80657-64-3) | 1470 | 10 | 243 |
| Verdox (cas # 88-41-5) | 1319 | 10 | 221 |
| Flor Acetate (cas # 5413-60-5) | 1442 | 11 | 175 |
| Orange Terpenes (cas # 68917-57-7) | 1040 | 10 | 176 |

Example 3

A shade is prepared as in Example 2, except that the volatile composition is that which is described in Table 2 (wherein greater than 80% by weight of the volatile composition's ingredients have a KI value of less than about 1700). After about 6 hours, about 20% w/w of the perfume originally in the shade at the time of removal from the metalized bag is evaporated from the shade.

TABLE 2

Composition of Volatile Composition of Example 3

| Material Name | Approximate KI Value | % w/w | Approximate Boiling Point (° C.) |
|---|---|---|---|
| Aurantiol (cas # 89-43-0) | 2294 | 2 | 413 |
| Benzyl Salicylate (cas # 118-58-1) | 2139 | 3 | 320 |
| Coumarin (cas # 91-64-5) | 1463 | 1 | 300 |
| Ethyl Vanillin (cas # 121-32-4) | 1652 | 4 | 285 |
| Hexyl Cinnamic Aldehyde (cas # 101-86-0) | 1770 | 3 | 334 |
| Iso E Super (cas # 54464-57-2) | 1706 | 5 | 307 |
| Linalool (cas # 78-70-6) | 1243 | 7 | 195 |
| Linalyl Acetate (cas # 115-95-7) | 1262 | 3 | 220 |
| Methyl Dihydro Jasmonate (cas # 24851-98-7) | 1668 | 9 | 300 |
| Polysantol (cas # 107898-54-4) | 1703 | 2 | 295 |
| Silvanone Ci (mixture)[1] | 1984 | 4 | 300 |
| Vanillin (cas # 121-33-5) | 1589 | 3 | 285 |
| Dipropylene Glycol (cas # 110-98-5) | 1152 | 3 | 231 |
| Dipropylene Glycol Methyl Ether (cas # 34590-94-8) | 997 | 50 | 190 |

[1]Silvanone Ci is available from Quest International of Mount Olive, New Jersey.

Example 4

A shade is prepared using SYNERGEX 6130 manufactured by BBA/Fiberweb of Simpsonville, S.C. The SYNERGEX material is comprised of calendered polyester fibers with a basis weight of 102 g/m$^2$ and a thickness of 0.3 mm. The material is folded and cut to form a tube having a circumference of 190 mm and a height of 190 mm. The seam of the tube is secured by applying transfer adhesive tape (sold as 9471LE available from 3M Corporation of St. Paul, Minn.) to an approximate 0.5 inch (1.3 cm) overlap. The tube is then creased to form a flat structure.

About 0.7 g of the volatile composition described in Table 3 (wherein only about 62% by weight of the volatile composition's ingredients have a KI value of less than about 1700) is applied to the tubular shade. The tubular shade is then promptly placed into a metalized 2.2 mil poly bag (0.055 mm) (available as Part No. S-6176 from U-Line Corporation) and heat sealed.

After approximately 4 hours the tubular shade is removed from the metalized poly bag and opened to a tube shape and placed into a room having a temperature of approximately 70° F. (21° C.). After about 5 hours, about 20% w/w of the perfume originally in the shade at the time of removal from the metalized bag is evaporated from the shade. After about 24 hours, about 30% w/w of the perfume originally in the shade at the time of removal from the metalized bag is evaporated from the shade.

TABLE 3

Composition of Volatile Composition of Example 4

| Material Name | Approximate KI Value | % w/w | Approximate Boiling Point (° C.) |
|---|---|---|---|
| Aurantiol (cas # 89-43-0) | 2294 | 3.800 | 260 |
| Benzyl Salicylate (cas # 118-58-1) | 2139 | 6.830 | 300 |
| Coumarin (cas # 91-64-5) | 1463 | 2.780 | 300 |
| Ethyl Vanillin (cas # 121-32-4) | 1652 | 7.590 | 285 |
| Hexyl Cinnamic Aldehyde (cas # 101-86-0) | 1770 | 6.070 | 305 |
| Iso E Super (cas # 54464-57-2) | 1706 | 10.120 | 230 |
| Linalool (cas # 78-70-6) | 1243 | 14.930 | 195 |
| Linalyl Acetate (cas # 115-95-7) | 1262 | 5.110 | 220 |
| Methyl Dihydro Jasmonate (cas # 24851-98-7) | 1668 | 18.980 | 300 |
| Polysantol (cas # 107898-54-4) | 1703 | 3.800 | 295 |
| Silvanone Ci (mixture)[1] | 1984 | 7.590 | 300 |
| Vanillin (cas # 121-33-5) | 1589 | 6.070 | 285 |
| Dipropylene Glycol (cas # 110-98-5) | 1152 | 6.330 | 231 |

[1]Silvanone Ci is available from Quest International of Mount Olive, New Jersey.

Example 5

A shade is prepared using SYNERGEX 6130 manufactured by BBA/Fiberweb of Simpsonville, S.C. The SYNERGEX material is comprised of calendared polyester fibers having a basis weight of 102 gsm and a thickness of 0.3 mm. The material is folded and cut to form a tube having a circumference of 190 mm and a height of 220 mm. The seam of the tube is secured by applying transfer adhesive tape (sold as 9471LE and available from 3M Corporation of St. Paul, Minn.) to an approximate 0.5 inch (1.3 cm) overlap. The tube is then creased to form a flat structure.

0.7 g of the volatile composition described in Table 2 is applied to the tubular shade. The tubular shade is then promptly placed into a metalized 2.2 mil (0.055 mm) poly bag (available as Part No. S-6176 from U-Line Corporation) and heat sealed.

After approximately 24 hours the tubular shade is removed from the metalized poly bag and opened into a tube shape and placed into a room having a temperature of approximately 70° F. (21° C.). After about 5 hours, more than about 50% w/w of the perfume originally in the shade at the time of removal from the metalized bag is evaporated from the shade. After about 24 hours, more than about 65% w/w of the perfume originally in the shade at the time of removal from the metalized bag is evaporated from the shade.

Example 6

A shade is prepared using SYNERGEX 6130 manufactured by BBA/Fiberweb of Simpsonville, S.C. The SYNERGEX material is comprised of calendared polyester fibers with a basis weight of 102 gsm and a thickness of 0.3 mm. The material is folded and cut to form a tube having a circumference of 190 mm and a height of 220 mm. The seam of the tube is secured by applying transfer adhesive tape (sold as 9471LE available from 3M Corporation of St. Paul, Minn.) to an approximate 0.5 inch (1.3 cm) overlap. The tube is then creased to form a flat structure.

0.7 g of the volatile composition described in Table 1 is applied to the tubular shade. The tubular shade is then immediately placed into a metalized 2.2 mil (0.055 mm) thickness poly bag available as Part No. S-6176 from U-Line Corporation and heat sealed.

After approximately 24 hours the tubular shade is removed from the metalized poly bag and opened to a tube shape and placed into a room having a temperature of approximately 70° F. (21° C.). After about 5 hours, about 80% w/w of the perfume originally in the shade at the time of removal from the metalized bag is evaporated from the shade. After about 24 hours, more than about 85% w/w of the perfume originally in the shade at the time of removal from the metalized bag is evaporated from the shade.

Example 7

A translucent paper sold by CTI Paper USA, of Sun Prairie Wis., under the name "Parchment White Glama Natural" having a nominal basis weight of 110 g/m² is folded and cut to form a tube having a circumference of 190 mm and a height of 220 mm. The seam of the tube is secured by applying transfer adhesive tape (sold as 9471LE and available from 3M Corporation of St. Paul, Minn.) to an approximate 0.5 inch (1.3 cm) overlap. The tube is then creased to form a flat structure.

A strip of absorbent material (sold as product No. 7620W available from EMI Specialty Papers of Redding, Conn.) is cut to about 1.7 cm by 19 cm and secured to the inside of the paper tube very near the end of the tube using a double sided tape (sold as product No. 9500PC available from 3M Corporation).

Approximately 0.45 g of a volatile composition having the composition shown in Table 1 (wherein greater than 90% by weight of the volatile composition's ingredients have a KI value of less than about 1500) is applied to the absorbent strip of material using a transfer pipette. The tube is then placed into a metalized poly bag (available from ULine Corporation as Part No. S-6176) and heat sealed.

After approximately 48 hours the tube is removed from the metalized poly bag and opened into a tube shape and placed into a room having a temperature of approximately 70° F. (21° C.). The tube is placed vertically on a table with the absorbent strip at the top of the tube. After about 6 hours, about 50% w/w of the perfume in the shade at the time of removal from the metalized bag is evaporated from the shade. After about 24 hours, about 65% w/w of the perfume originally in the shade at the time of removal from the metalized bag is evaporated from the shade.

Example 8

A shade is prepared using SYNERGEX 6130 manufactured by BBA/Fiberweb of Simpsonville, S.C. The SYNERGEX material is comprised of calendared polyester fibers with a basis weight of 102 g/m² and a thickness of 0.3 mm. The average pore size diameter of this material is approximately 34 microns with a range of about 10 microns to about 75 microns. The material is printed with a graphical pattern using conventional inks with an inkjet printer. The SYNERGEX material is then cut to a dimension of 19 cm by 20 cm and rolled into a tube and sealed along the 19 cm length with a 1 cm overlap. The SYNERGEX material is heat sealed to itself using a VERTROD brand impulse heat sealer. The opacity of the shade when dry prior to perfume addition is measured to be 65% dry using a Hunter Labscan XE. The shade is loaded with 0.7 grams of the perfume composition shown in Table 1. Promptly after loading the shade with the perfume the opacity is measured and is found to be 43%. Four hours after application of the perfume composition to the shade 50% of the perfume is evaporated and the opacity is increased to 55%.

Example 9

A shade is prepared as in Example 2. Before sealing into the metalized poly bag, a decorative design in the shape of a flower is drawn on the outside of the shade using a "Disappearing Ink Marking Pen" available from Pyrm-Dritz Corporation of Spartanburg, S.C. The decorative design disappears from the shade within about 24 hours after removal from the metalized bag.

Example 10

A flexible sheet article is constructed by adhesive laminating a layer of translucent paper sold by CTI Paper USA, of Sun Prairie Wis., under the name "Parchment White Glama Natural" with a nominal basis weight of 110 g/m² to a layer of microporous high molecular weight polyethylene sold by DSM Solutech of Heerlen, Netherlands under the name SOLUPOR 7PO3A with a nominal basis weight of 7 g/m². The translucent paper is printed with decorative graphics using an HP inkjet printer. The laminated structure is then cut to 200 mm×185 mm and rolled along the 200 mm width with a 10 mm overlap to create an oval shaped tube with circumference of 190 mm with a 185 mm height. The flexible article is rolled such that the microporous polyethylene is on the outside and the translucent paper with graphics printed is on the inside. A layer of double sided tape from 3M Corporation (available as 3M 9471 LE) is used in the overlap region to keep the tube from unrolling.

Approximately 2 ml of a volatile composition having the composition described in Table 1 is applied to the flexible tube article. The flexible article is then placed in a high barrier pouch and sealed to keep the article from losing the volatile composition until ready to be used. The flexible tube article can be used as a standalone air freshener or can be placed on a base to help hold the article upright. Alternatively the article can also be used as a luminary shade when placed over a light base.

Samples of the laminated structure are cut and the opacity is measured before and after wetting with the volatile composition. The dry structure has an opacity of 95% and the wetted structure has an opacity of 45%. When dry the tube article or luminary shade is white in appearance due to the opacity of the microporous polyethylene. When wet the microporous polyethylene is semi-transparent and the graphics on the inside can be seen very clearly both with and without illumination on the inside of the tube. As the volatile composition evaporates over a 10 hour time period the shade becomes more opaque and within 2 days is back to the original 95% opacity with very little graphic visible. This change in appearance helps communicate to a user that the fragrance has been substantially depleted and can now be discarded and replaced with a new shade.

Example 11

A flexible article is constructed with the same materials as described in Example 10 but the microporous polyethylene is printed with graphics instead of the translucent paper and the laminated structure is rolled into a tube such that the printed microporous PE is on the inside with the printed surface of the tube and the unprinted translucent paper is on the outside.

The flexible article is again wetted with the same volatile composition as used in Table 1 but now the volatile composition is on the inside of the tube. The opacity of the article went from 95% when dry to 45% when wet and again the graphics were highly visible when wet but were hidden due to the opacity change of the microporous polyethylene material. With this example the release rate of the volatile composition is slower due to the wetted microporous polyethylene being on the inside versus the outside of the oval tube shape. The perfume is released over a period of 5 days.

Example 12

Three shades are prepared using a multi-layer structure. The venting of the shades is adjusted to determine the effect of perfume evaporation rate. The shades are constructed of three layers. The outer layer is a 60 gsm heat sealable paper from Ahlstrom Windsor Locks LLC of Windsor Locks, Conn. The middle barrier layer is comprised of a blown PE/EVOH/PE 2.5 mil thick film available from Printpak Incorporated of Atlanta, Ga. The inner layer is comprised of a 102 gsm spunbond polyester nonwoven with the tradename of SYNERGEX 6130 available from BBA/Fiberweb os Simpsonville, S.C. The SYNERGEX material is comprised of calendared polyester fibers having a thickness of 0.3 mm. The three layers are laminated together using a hot roll laminator with a roll pressure of 60 psi, a roll temperature of 360° F. (182° C.) and a speed setting of 20. The tri-layer sheet is then die cut to the dimensions of 185 mm×200 mm using a hydraulic press and a steel rule die. The 185 mm×200 mm sheet is then folded around a folding board that is 185 mm long by 95 mm wide with the SYNERGEX absorbent material on the inside. The shade is then sealed along the 185 mm length at the overlap using a lap seam. This creates a flattened tube that is 185 mm long with a circumference of approximately 192 mm (having an 8 mm overlap). The sealing is done with an impulse heat sealer model No. 24LABMod S/N:V-49093 with a bar pressure of 50 psi, a heat pulse dwell of 8 seconds, and a cool dwell of 16 seconds. The power setting to heat the impulse metal ribbon is set at 27.5 on the dial.

The inside (SYNERGEX layer) of the formed shades are dosed with 0.5 grams of a cucumber and melon perfume available from International Flavors and Fragrances of Hazlet, N.J. The shades are then placed on an oval shaped base to hold the shade upright with the shade tube opening facing upward and the other opening fitting snuggly in the oval base.

Two different types of thermoformed bases are used to hold the shades. One base has a closed bottom such that the shade fits tightly into the base with little to no possibility for air to move through the base and/or between the interface between the base and the shade. This is designated the "no venting base". The other base has two 0.75 inch (19 mm) diameter holes in the center of the base with an equivalent 1 square inch (6.45 cm$^2$) area openings on the sides of the base. This is designated the "venting base" with an equivalent of 1 square inch (6.45 cm$^2$) of area for air to flow through the base (sidewalls and top) and hence the bottom of the shade.

The top of the shades are adjusted to be either open or closed using a paper clip to close them shut and a 35 mm diameter thin ring to open the shade. Optionally a foil tape can be applied on the top of the shade to help the shade stay opened or closed to a desired shape. The three shades are tested under three different conditions: 1) closed top and closed base; 2) open top and closed base; and 3) open top of shade and open base. The perfume evaporation rate is measured by weighing the shades at different time intervals and taking the difference over the time interval to calculate the average weight loss/hour. The results which are shown in Table 4 below illustrate how the open top with the closed bottom increases the evaporation and how the evaporation is further increased when the vented base is used in conjunction with the top and bottom of the shade being vented.

TABLE 4

Perfume Release Rate over 6.7 Hours
(Average mg of Perfume Released per Hour of Time Elapsed)

| Time Elapsed (Hours) | Closed Base and Closed Top of Shade (Approx. mg/hour) | Closed Base and Open Top using 35 mm Spacer (Approx. mg/hour) | Vented Base and Open Top Using 35 mm Spacer (Approx. mg/hour) |
|---|---|---|---|
| 0-1 | 3.0 | 18.8 | 103.8 |
| 1-2.7 | 3.0 | 21.4 | 59.4 |
| 2.7-3.2 | 2.0 | 17.1 | 40.0 |
| 3.2-3.7 | 3.0 | 18.8 | 40.0 |
| 3.7-5.2 | 2.0 | 19.0 | 27.9 |
| 5.2-6.7 | 3.0 | 9.8 | 32.6 |

Example 13

An integral shade and package are made to demonstrate how a low cost all-in-one scented product and package can be made. The shade is made by taking a bi-laminate substrate comprising an absorbent non-woven laminated to a barrier film. SYNERGEX 6125 PET non-woven described previously is used for the inner absorbent layer. The outer barrier film is a film supplied by Printpak of Atlanta, Ga. consisting of PET/PE/EVOH/PE. The barrier film is thermally laminated to the SYNERGEX non-woven in a similar manner as described in Example 12 with the exception that the SYNERGEX is 0.5 inches (1.3 cm) narrower on the top and bottom (see FIG. 20) leaving regions with no absorbent material present. This narrower width of the non-woven is done so the non-woven is not in the seal region. The non-woven is then loaded with 1 gram of perfume as described in Table 1 of Example 2. The bi-laminate is then folded on itself with the perfumed non-woven on the inside and the barrier film facing outward. The barrier film is then heat sealed to itself on the 3 open ends. The sealed package can be opened by using scissors and cutting off the seal region on two ends. Alternatively or in addition, the barrier film can be laser scored to aid in easily tearing off the ends. The opened package can be formed into a cube shape and inserted on a base to allow scent release. This style of all-in-one package and shade all in one can be made using a vertical or horizontal form/fill/seal machine such as manufactured by Hayssen Packaging Technologies of Duncan, S.C.

Example 14

An integral shade and package are made in the same manner as described in Example 13 except the absorbent material is product No. 7620W available from EMI Specialty Papers of Redding, Conn. instead of the SYNERGEX 6125. This thicker more absorbent material is then dosed with 7 ml of perfume and sealed in the same manner as described in Example 13. This shade is opened by removing the sealed ends and opening to form a cube-like shape. This example illustrates how a longer lasting low cost air freshener could be produced. To provide a faster scent release the cube can be placed on some small blocks to allow air to flow through the cube.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. All documents cited herein are in relevant part, incorporated by reference. The citation of any document is not to be construed as an admission that it is prior art with respect to the present invention.

What is claimed is:

1. A decorative luminary, said decorative luminary comprising:
   a) a base, said base comprising a light source; and
   b) a disposable shade wherein said shade is impregnated with a composition wherein from about 50% to about 100% is comprised of a volatile composition wherein said volatile composition includes at least one ingredient which has a Kovat's Index from about 600 to about 1800.

2. A decorative luminary, said decorative luminary comprising:
   a) a base, said base comprising a light source; and
   b) a disposable shade wherein said shade is impregnated with a volatile composition comprising perfume ingredients wherein said perfume ingredients are selected from a first group of ingredients having a boiling point of about 20° C. to about 250° C. and a ClogP value from about −2 to about 3; a second group of ingredients having a boiling point of about 20° C. to about 250° C. and a ClogP value from about 3 to about 9; a third group of ingredients having a boiling point of about 250° C. to about 400° C. and a ClogP value from about −2 to about 3; a fourth group of ingredients having a boiling point of about 250° C. to about 400° C. and a ClogP of about 3 to about 9; or a combination thereof.

3. A decorative luminary, said decorative luminary comprising:
   a disposable shade wherein said shade includes a volatile composition wherein said volatile composition is about 50% or more depleted from the shade within about twenty-four hours after said shade is exposed to air.

4. A composition for a decorative luminary, said composition comprising:
   a volatile composition wherein said volatile composition is provided in an amount capable of adding from about 60 milligrams to about 15 grams of said volatile composition to a shade wherein said volatile composition prior to addition to said shade is contained in an ampoule, a pouch, a dropper bottle, a sachet, a spray, a blow-fill seal container, or a combination thereof and wherein said volatile composition has a Kovat's Index of about 600 to about 1800.

5. The composition of claim 4 wherein said composition further comprises perfume ingredients wherein said perfume ingredients are selected from: a first group of ingredients having a boiling point of about 20° C. to about 250° C. and a ClogP value from about −2 to about 3; a second group of ingredients having a boiling point of about 20° C. to about 250° C. and a ClogP value from about 3 to about 9; a third group of ingredients having a boiling point of about 250° C. to about 400° C. and a ClogP value from about −2 to about 3; a fourth group of ingredients having a boiling point of about 250° C. to about 400° C. and a ClogP of about 3 to about 9; or a combination thereof.

* * * * *